(12) United States Patent
Jenson et al.

(10) Patent No.: US 8,241,315 B2
(45) Date of Patent: Aug. 14, 2012

(54) APPARATUS AND METHOD FOR TREATING OCCLUDED VASCULATURE

(75) Inventors: Mark L. Jenson, Greenfield, MN (US); William J. Drasler, Minnetonka, MN (US); Daniel M. Lafontaine, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2759 days.

(21) Appl. No.: 10/877,340

(22) Filed: Jun. 24, 2004

(65) Prior Publication Data

US 2005/0288695 A1    Dec. 29, 2005

(51) Int. Cl.
*A61M 29/00* (2006.01)
(52) U.S. Cl. ....................................................... 606/194
(58) Field of Classification Search .................. 606/194, 606/1.11, 159, 185, 186, 191, 192; 600/184; 623/1.11; 604/22, 164.1, 164.11, 164.13, 604/165.01, 165.02, 264
See application file for complete search history.

(56) References Cited

U.S. PATENT DOCUMENTS

| | | |
|---|---|---|
| 3,472,230 A | 10/1969 | Fogarty |
| 3,592,186 A | 7/1971 | Oster |
| 3,683,904 A | 8/1972 | Forster |
| 3,889,657 A | 6/1975 | Baumgarten |
| 3,952,747 A | 4/1976 | Kimmell, Jr. |
| 3,996,938 A | 12/1976 | Clark, III |
| 4,046,150 A | 9/1977 | Schwartz et al. |
| 4,425,908 A | 1/1984 | Simon |
| 4,447,227 A | 5/1984 | Kotsanis |
| 4,580,568 A | 4/1986 | Gianturco |
| 4,590,938 A | 5/1986 | Segura et al. |
| 4,619,246 A | 10/1986 | Molgaard-Nielsen et al. |
| 4,631,052 A | 12/1986 | Kensey |
| 4,643,184 A | 2/1987 | Mobin-Uddin |
| 4,650,466 A | 3/1987 | Luther |
| 4,662,885 A | 5/1987 | DiPisa, Jr. |
| 4,705,517 A | 11/1987 | DiPisa, Jr. |
| 4,706,671 A | 11/1987 | Weinrib |
| 4,723,549 A | 2/1988 | Wholey et al. |
| 4,728,319 A | 3/1988 | Masch |
| 4,733,665 A | 3/1988 | Palmaz |

(Continued)

FOREIGN PATENT DOCUMENTS

DE        28 21 048           7/1980

(Continued)

OTHER PUBLICATIONS

"Atherosclerotic Disease of the Aortic Arch as a Risk Factor of Recurrent Ischemic Stroke," *The New England Journal of Medicine*, vol. 334, No. 19, May 9, 1996, pp. 1216-1221.

(Continued)

*Primary Examiner* — Gary Jackson
*Assistant Examiner* — Jonathan Hollm
(74) *Attorney, Agent, or Firm* — Seager, Tufte & Wickhem, LLC

(57) ABSTRACT

Occluded vasculature such as occluded arterial vasculature can be recanalized using a device that is configured to penetrate an occlusion, while limiting a distance that said penetration structure can extend in order to limit inadvertent vascular damage. The device can include an elongate sheath and a stylet disposed within the elongate sheath. The elongate sheath and the stylet can include, in combination, an engagement section that is configured to limit relative axial movement between the elongate sheath and the stylet.

9 Claims, 21 Drawing Sheets

U.S. PATENT DOCUMENTS

| | | | |
|---|---|---|---|
| 4,749,376 A | 6/1988 | Kensey et al. | |
| 4,790,812 A | 12/1988 | Hawkins, Jr. et al. | |
| 4,790,813 A | 12/1988 | Kensey | |
| 4,794,928 A | 1/1989 | Kletschka | |
| 4,794,931 A | 1/1989 | Yock | |
| 4,800,882 A | 1/1989 | Gianturco | |
| 4,807,626 A | 2/1989 | McGirr | |
| 4,824,435 A | 4/1989 | Giesy et al. | |
| 4,842,579 A | 6/1989 | Shiber | |
| 4,857,045 A | 8/1989 | Rydell | |
| 4,857,046 A | 8/1989 | Stevens et al. | |
| 4,867,157 A | 9/1989 | McGurk-Burleson et al. | |
| 4,873,978 A | 10/1989 | Ginsburg | |
| 4,898,575 A * | 2/1990 | Fischell et al. | 604/22 |
| 4,907,336 A | 3/1990 | Gianturco | |
| 4,921,478 A | 5/1990 | Solano et al. | |
| 4,921,484 A | 5/1990 | Hillstead | |
| 4,926,858 A | 5/1990 | Gifford, III et al. | |
| 4,950,277 A | 8/1990 | Farr | |
| 4,955,895 A | 9/1990 | Sugiyama et al. | |
| 4,957,482 A | 9/1990 | Shiber | |
| 4,969,891 A | 11/1990 | Gewertz | |
| 4,979,951 A | 12/1990 | Simpson | |
| 4,986,807 A | 1/1991 | Farr | |
| 4,998,539 A | 3/1991 | Delsanti | |
| 5,002,560 A | 3/1991 | Machold et al. | |
| RE33,569 E | 4/1991 | Gifford, III et al. | |
| 5,007,896 A | 4/1991 | Shiber | |
| 5,007,917 A | 4/1991 | Evans | |
| 5,011,488 A | 4/1991 | Ginsburg | |
| 5,019,088 A | 5/1991 | Farr | |
| 5,041,082 A * | 8/1991 | Shiber | 604/22 |
| 5,041,126 A | 8/1991 | Gianturco | |
| 5,053,008 A | 10/1991 | Bajaj | |
| 5,053,044 A | 10/1991 | Mueller et al. | |
| 5,061,245 A | 10/1991 | Waldvogel | |
| 5,071,407 A | 12/1991 | Termin et al. | |
| 5,071,425 A | 12/1991 | Gifford, III et al. | |
| 5,085,662 A | 2/1992 | Willard | |
| 5,087,265 A | 2/1992 | Summers | |
| 5,100,423 A | 3/1992 | Fearnot | |
| 5,100,424 A | 3/1992 | Jang et al. | |
| 5,100,425 A | 3/1992 | Fischell et al. | |
| 5,102,403 A | 4/1992 | Alt | |
| 5,102,415 A | 4/1992 | Guenther et al. | |
| 5,104,399 A | 4/1992 | Lazarus | |
| 5,106,376 A | 4/1992 | Mononen et al. | |
| 5,108,419 A | 4/1992 | Reger et al. | |
| 5,133,733 A | 7/1992 | Rasmussen et al. | |
| 5,135,531 A | 8/1992 | Shiber | |
| 5,152,771 A | 10/1992 | Sabbaghian et al. | |
| 5,152,777 A | 10/1992 | Goldberg et al. | |
| 5,160,342 A | 11/1992 | Reger et al. | |
| 5,171,233 A | 12/1992 | Amplatz et al. | |
| 5,190,528 A | 3/1993 | Fonger et al. | |
| 5,190,546 A | 3/1993 | Jervis | |
| 5,195,955 A | 3/1993 | Don Michael | |
| 5,224,953 A | 7/1993 | Morgentaler | |
| 5,231,989 A | 8/1993 | Middleman et al. | |
| 5,232,442 A * | 8/1993 | Johnson et al. | 604/506 |
| 5,267,955 A | 12/1993 | Hanson | |
| 5,306,286 A | 4/1994 | Stack et al. | |
| 5,314,444 A | 5/1994 | Gianturco | |
| 5,314,472 A | 5/1994 | Fontaine | |
| 5,318,576 A | 6/1994 | Plassche, Jr. et al. | |
| 5,329,942 A | 7/1994 | Gunther et al. | |
| 5,330,484 A | 7/1994 | Gunther | |
| 5,330,500 A | 7/1994 | Song | |
| 5,350,398 A | 9/1994 | Pavcnik et al. | |
| 5,354,310 A | 10/1994 | Garnic et al. | |
| 5,356,423 A | 10/1994 | Tihon et al. | |
| 5,366,464 A | 11/1994 | Belknap | |
| 5,366,473 A | 11/1994 | Winston et al. | |
| 5,370,657 A | 12/1994 | Irie | |
| 5,370,683 A | 12/1994 | Fontaine | |
| 5,376,100 A | 12/1994 | Lefebvre | |
| 5,383,887 A | 1/1995 | Nadal | |
| 5,383,892 A | 1/1995 | Cardon et al. | |
| 5,383,926 A | 1/1995 | Lock et al. | |
| 5,387,235 A | 2/1995 | Chuter | |
| 5,395,349 A | 3/1995 | Quiachon et al. | |
| 5,397,345 A | 3/1995 | Lazerus | |
| 5,405,377 A | 4/1995 | Cragg | |
| 5,409,454 A | 4/1995 | Fischell et al. | |
| 5,415,630 A | 5/1995 | Gory et al. | |
| 5,417,703 A | 5/1995 | Brown et al. | |
| 5,419,774 A | 5/1995 | Willard et al. | |
| 5,421,832 A | 6/1995 | Lefebvre | |
| 5,423,742 A | 6/1995 | Theron | |
| 5,423,846 A | 6/1995 | Fischell | |
| 5,423,885 A | 6/1995 | Williams | |
| 5,425,765 A | 6/1995 | Tiefenbrun et al. | |
| 5,431,673 A | 7/1995 | Summers et al. | |
| 5,443,498 A | 8/1995 | Fontaine | |
| 5,449,372 A | 9/1995 | Schmaltz et al. | |
| 5,456,667 A | 10/1995 | Ham et al. | |
| 5,462,529 A | 10/1995 | Simpson et al. | |
| 5,476,104 A | 12/1995 | Sheahon | |
| 5,484,418 A | 1/1996 | Quiachon et al. | |
| 5,499,973 A | 3/1996 | Saab | |
| 5,507,767 A | 4/1996 | Maeda et al. | |
| 5,512,044 A | 4/1996 | Duer | |
| 5,527,292 A | 6/1996 | Adams et al. | |
| 5,527,354 A | 6/1996 | Fontaine et al. | |
| 5,536,242 A | 7/1996 | Willard et al. | |
| 5,540,707 A | 7/1996 | Ressemann et al. | |
| 5,549,626 A | 8/1996 | Miller et al. | |
| 5,562,724 A | 10/1996 | Vowerk et al. | |
| 5,569,274 A | 10/1996 | Rapacki et al. | |
| 5,569,275 A | 10/1996 | Kotula et al. | |
| 5,628,761 A | 5/1997 | Rizik | |
| 5,634,897 A | 6/1997 | Dance et al. | |
| 5,658,296 A | 8/1997 | Bates et al. | |
| 5,662,671 A | 9/1997 | Barbut et al. | |
| 5,669,933 A | 9/1997 | Simon et al. | |
| 5,695,519 A | 12/1997 | Summers et al. | |
| 5,709,704 A | 1/1998 | Nott et al. | |
| 5,720,764 A | 2/1998 | Naderlinger | |
| 5,728,066 A | 3/1998 | Daneshvar | |
| 5,730,734 A | 3/1998 | Adams et al. | |
| 5,746,758 A | 5/1998 | Nordgren et al. | |
| 5,749,848 A | 5/1998 | Jang et al. | |
| 5,769,816 A | 6/1998 | Barbut et al. | |
| 5,779,716 A | 7/1998 | Cano et al. | |
| 5,792,300 A | 8/1998 | Inderbitzen et al. | |
| 5,795,322 A | 8/1998 | Boudewijn | |
| 5,797,952 A | 8/1998 | Klein | |
| 5,800,457 A | 9/1998 | Gelbfish | |
| 5,800,525 A | 9/1998 | Bachinski et al. | |
| 5,810,874 A | 9/1998 | Lefebvre | |
| 5,814,064 A | 9/1998 | Daniel et al. | |
| 5,817,102 A | 10/1998 | Johnson et al. | |
| 5,827,324 A | 10/1998 | Cassell et al. | |
| 5,833,604 A | 11/1998 | Houser et al. | |
| 5,833,644 A | 11/1998 | Zadno-Azizi et al. | |
| 5,833,650 A | 11/1998 | Imran | |
| 5,836,868 A | 11/1998 | Ressemann et al. | |
| 5,843,022 A | 12/1998 | Willard et al. | |
| 5,846,260 A | 12/1998 | Maahs | |
| 5,848,964 A | 12/1998 | Samuels | |
| 5,876,367 A | 3/1999 | Kaganov et al. | |
| 5,891,112 A | 4/1999 | Samson | |
| 5,893,867 A | 4/1999 | Bagaoisan et al. | |
| 5,895,399 A | 4/1999 | Barbut et al. | |
| 5,902,263 A | 5/1999 | Patterson et al. | |
| 5,906,594 A * | 5/1999 | Scarfone et al. | 604/165.01 |
| 5,906,618 A | 5/1999 | Larson, III | |
| 5,908,395 A | 6/1999 | Stalker et al. | |
| 5,908,435 A | 6/1999 | Samuels | |
| 5,910,154 A | 6/1999 | Tsugita et al. | |
| 5,911,734 A | 6/1999 | Tsugita et al. | |
| 5,916,193 A | 6/1999 | Stevens et al. | |
| 5,921,958 A | 7/1999 | Ressemann et al. | |
| 5,925,016 A | 7/1999 | Chornenky et al. | |
| 5,925,060 A | 7/1999 | Forber | |
| 5,925,062 A | 7/1999 | Purdy | |
| 5,925,063 A | 7/1999 | Khosravi | |

| | | | |
|---|---|---|---|
| 5,928,203 A | 7/1999 | Davey et al. | |
| 5,928,218 A | 7/1999 | Gelbfish | |
| 5,934,284 A | 8/1999 | Plaia et al. | |
| 5,935,108 A * | 8/1999 | Katoh et al. | 604/164.11 |
| 5,935,139 A | 8/1999 | Bates | |
| 5,938,645 A | 8/1999 | Gordon | |
| 5,938,671 A | 8/1999 | Katoh et al. | |
| 5,941,869 A | 8/1999 | Patterson et al. | |
| 5,941,896 A | 8/1999 | Kerr | |
| 5,947,995 A | 9/1999 | Samuels | |
| 5,951,585 A | 9/1999 | Cathcart et al. | |
| 5,954,745 A | 9/1999 | Gertler et al. | |
| 5,976,172 A | 11/1999 | Homsma et al. | |
| 5,989,210 A | 11/1999 | Morris et al. | |
| 5,989,271 A | 11/1999 | Bonnette et al. | |
| 5,989,281 A | 11/1999 | Barbut et al. | |
| 5,993,469 A | 11/1999 | McKenzie et al. | |
| 5,997,557 A | 12/1999 | Barbut et al. | |
| 6,001,118 A | 12/1999 | Daniel et al. | |
| 6,007,557 A | 12/1999 | Ambrisco et al. | |
| 6,010,522 A | 1/2000 | Barbut et al. | |
| 6,013,085 A | 1/2000 | Howard | |
| 6,027,520 A | 2/2000 | Tsugita et al. | |
| 6,051,014 A | 4/2000 | Jang | |
| 6,053,932 A | 4/2000 | Daniel et al. | |
| 6,059,814 A | 5/2000 | Ladd | |
| 6,068,645 A | 5/2000 | Tu | |
| 6,086,605 A | 7/2000 | Barbut et al. | |
| 6,120,516 A | 9/2000 | Selmon et al. | |
| 6,129,739 A | 10/2000 | Khosravi | |
| 6,142,987 A | 11/2000 | Tsugita | |
| 6,152,946 A | 11/2000 | Broome et al. | |
| 6,165,200 A | 12/2000 | Tsugita et al. | |
| 6,168,579 B1 | 1/2001 | Tsugita | |
| 6,171,327 B1 | 1/2001 | Daniel et al. | |
| 6,179,851 B1 | 1/2001 | Barbut et al. | |
| 6,179,859 B1 | 1/2001 | Bates et al. | |
| 6,179,861 B1 | 1/2001 | Khosravi et al. | |
| 6,183,432 B1 | 2/2001 | Milo | |
| 6,193,735 B1 | 2/2001 | Stevens | |
| 6,203,561 B1 | 3/2001 | Ramee et al. | |
| 6,210,377 B1 * | 4/2001 | Ouchi | 604/264 |
| 6,210,378 B1 | 4/2001 | Ouchi | |
| 6,214,026 B1 | 4/2001 | Lepak et al. | |
| 6,217,527 B1 | 4/2001 | Selmon et al. | |
| 6,221,049 B1 | 4/2001 | Selmon et al. | |
| 6,231,546 B1 | 5/2001 | Milo et al. | |
| 6,235,000 B1 | 5/2001 | Milo et al. | |
| 6,254,573 B1 | 7/2001 | Haim et al. | |
| 6,258,052 B1 | 7/2001 | Milo | |
| 6,266,550 B1 | 7/2001 | Selmon et al. | |
| 6,290,689 B1 | 9/2001 | Delaney et al. | |
| 6,290,709 B1 * | 9/2001 | Ellis et al. | 606/167 |
| 6,416,523 B1 | 7/2002 | Lafontaine | |
| 6,428,552 B1 | 8/2002 | Sparks | |
| 6,447,525 B2 | 9/2002 | Follmer et al. | |
| 6,506,178 B1 | 1/2003 | Schubart et al. | |
| 6,508,825 B1 | 1/2003 | Selmon et al. | |
| 6,511,458 B2 | 1/2003 | Milo et al. | |
| 6,527,979 B2 | 3/2003 | Constantz et al. | |
| 6,533,767 B2 | 3/2003 | Johansson et al. | |
| 6,599,304 B1 | 7/2003 | Selmon et al. | |
| 6,626,868 B1 * | 9/2003 | Prestidge et al. | 604/158 |
| 6,638,247 B1 | 10/2003 | Selmon et al. | |
| 2003/0023261 A1 | 1/2003 | Tomaschko et al. | |
| 2003/0167051 A1 | 9/2003 | Zhou | |

FOREIGN PATENT DOCUMENTS

| | | |
|---|---|---|
| DE | 34 17 738 | 11/1985 |
| DE | 40 30 998 A1 | 10/1990 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| FR | 2 580 504 | 10/1986 |
| FR | 2 643 250 A1 | 8/1990 |
| FR | 2 666 980 | 3/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/49793 A1 | 10/1999 |
| WO | WO 99/55236 | 11/1999 |
| WO | WO 99/58068 | 11/1999 |
| WO | WO 00/07655 | 2/2000 |
| WO | WO 00/09054 | 2/2000 |
| WO | WO 00/16705 | 3/2000 |
| WO | WO 00/49970 | 8/2000 |

OTHER PUBLICATIONS

"Endovascular Grafts, Stents Drive Interventional Radiology Growth," *Cardiovascular Device Update*, vol. 2, No. 3, Mar. 1996, pp. 1-12.

Cragg, Andrew et al., "A New Percutaneous Vena Cava Filter," *AJR*, vol. 141, Sep. 1983, pp. 601-604.

Cragg, Andrew et al., "Nonsurgical Placement of Arterial Endoprostheses: A New Technique Using Nitinol Wire," *Radiology*, vol. 147, No. 1, Apr. 1983, pp. 261-263.

Diethrich et al., "Percutaneous Techniques for Endoluminal Carotid Interventions," *J. Endovasc. Surg.*, vol. 3 (1996) pp. 182-202.

Fadali, A. Moneim et al., "A Filtering Device for the Prevention of Particulate Embolization During the Course of Cardiac Surgery," *Surgery*, vol. 64, No. 3, Sep. 1968, pp. 634-639.

Haissaguerre et al., "Spontaneous Initiation of Atrial Fibrillation by Ectopic Beats Originating in the Pulmonary Veins," *The New*

*England Journal of Medicine*, vol. 339, No. 10, Sep. 3, 1988, pp. 659-666.

Jordan, Jr. et al., "Microemboli Detected by Transcranial Doppler Monitoring in Patients During Carotid Angioplasty Versus Carotid Endarterectomy," *Cardiovascular Surgery*, vol. 7, No. 1, Jan. 1999, pp. 33-38.

Karalis, Dean G. et al., "Recognition and Embolic Potential of Intraaortic Atherosclerotic Debris," *Journal of the American College of Cardiology*, vol. 17, No. 1, Jan. 1991, pp. 73-78.

Lesh, "Can Catheter Ablation Cure Atrial Fibrillation?" *ACC Current Journal Review*, Sep./Oct. 1997, pp. 38-40.

Lund et al., "Long-Term Patency of the Ductus Arteriosus After Balloon Dilatation: an Experimental Study," *Circulation*, vol. 69, No. 4, Apr. 1984, pp. 772-774.

Marache et al., "Percutaneous Transluminal Venous Angioplasty in Occlusive Iliac Vein Thrombosis Resistant to Thromolysis," *American Heart Journal*, vol. 125, No. 2, Part 1, Feb. 1993, pp. 362-366.

Mazur et al., "Directional Atherectomy with the Omnicath™: A Unique New Catheter System," *Catheterization and Cardiovascular Diagnosis*, vol. 31, No. 1, Jan. 1994, pp. 79-84.

Moussa, Issaam et al. "Stents Don't Require Systemic Anticoagulation . . . But the Technique (and Results) Must be Optimal," *Journal of Invasive Cardiol.*, vol. 8, Suppl. E (1996) pp. 3E-7E.

Nakanishi et al., "Catheter Intervention to Venous System Using Expandable Metallic Stents," *Rinsho Kyobu Geka*, vol. 14, No. 2, Apr. 1994, 1 page, English Abstract Only.

Önal et al., "Primary Stenting for Complex Atherosclerotic Plaques in Aortic and Iliac Stenoses," *Cardiovascular & Interventional Radiology*, vol. 21, No. 5, Sep./Oct. 1998, pp. 386-392.

Theron et al., "New Triple Coaxial Catheter System for Carotid Angioplasty with Cerebral Protection," *American Journal of Neuroradiology*, vol. 11, Sep./Oct. 1990, pp. 869-874.

Tunick, Paul, A. et al. "Protruding Atheromas in the Thoracic Aortic and Systemic Embolization," *Annals of Internal Medicine*, vol. 115, No. 6, Sep. 15, 1991, pp. 423-427.

Tunick et al., "Protruding Atherosclerotic Plaque in the Aortic Arch of Patients with Systemic Embolization: A New Finding Seen by Transesophageal Echocardiography," *American Heart Journal*, vol. 120, No. 3, Sep. 1990, pp. 658-660.

Waksman et al., "Distal Embolization is Common After Directional Atherectomy in Coronary Arteries and Saphenous Vein Grafts," *American Heart Journal*, vol. 129, No. 3, Mar. 1995, pp. 430-435.

Wholey, Mark H. et al., PTA and Stents in the Treatment of Extracranial Circulation, *The Journal of Invasive Cardiology*, vol. 8, Suppl. E (1996) pp. 25E-30E.

\* cited by examiner

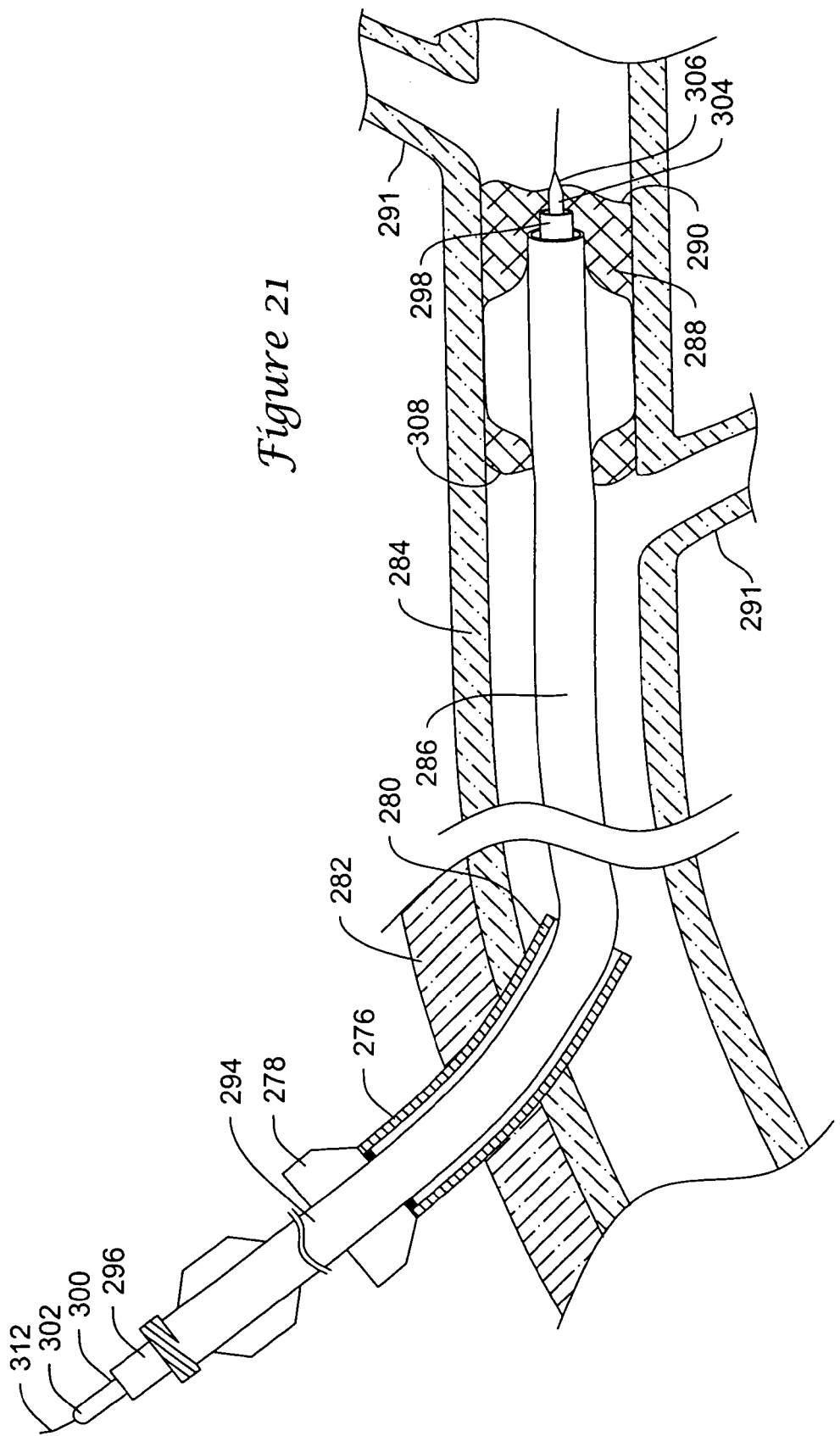

US 8,241,315 B2

APPARATUS AND METHOD FOR TREATING OCCLUDED VASCULATURE

TECHNICAL FIELD

The invention relates generally to medical devices and more specifically to medical devices configured for recanalization of occluded vasculature.

BACKGROUND

A number of patients suffer from vascular occlusions. Vascular occlusions can occur in the coronary arteries as well as in peripheral arteries such as those found in a patient's legs. Occlusions can be partial occlusions that reduce blood flow through the occluded portion of an artery. Occlusions can also be total occlusions, which substantially reduce or even completely eliminate blood flow through the occluded portion of the artery. Total occlusions such as chronic total occlusions can be difficult to traverse with existing catheters and guidewires, as they can include stiff or tough portions at their proximal and distal limits.

Physicians have attempted to cross or recanalize chronically totally occluded blood vessels such as arteries using a variety of devices and techniques. Unfortunately, many of these devices and techniques have relatively low success rates and relatively high rates of complications. A particular issue is penetrating a proximal cap of an occlusion without damaging the surrounding blood vessel, as proximal caps can have a curved or angled configuration that guides devices into the vessel wall or perhaps into a branch vessel.

Therefore, a need remains for a safe and effective way to penetrate and traverse occlusions such as chronic total occlusions. A need remains for a safe and effective way to penetrate and traverse difficult portions of an occlusion such as a proximal cap, which then allows traversing of the remainder of the occlusion with a conventional guidewire, catheter or other device.

SUMMARY

The invention is directed to apparatus and methods for recanalizing occluded vasculature such as occluded arterial vasculature. The invention provides a device that includes structure that is configured to penetrate an occlusion while limiting a distance that the penetration structure can extend in order to limit inadvertent vascular damage. Further, a preferred embodiment of the device provides means for centering the penetration into the proximal cap or other difficult portion of an occlusion. In preferred embodiments, the device provides means for advancement through the center of the occlusion.

Accordingly, an example embodiment of the invention can be found in an apparatus that includes an elongate sheath having a distal region, a proximal region and an inner surface defining a lumen extending therebetween. A stylet is disposed within the elongate sheath. The stylet includes a lumen extending from a distal region to a proximal region of the stylet. The elongate sheath and the stylet include, in combination, an engagement section that is configured to limit relative axial movement between the elongate sheath and the stylet.

Another example embodiment of the invention can be found in a recanalization assembly that includes a catheter having a distal region, a proximal region and a lumen extending therebetween. An elongate sheath is disposed within the catheter lumen and has a distal region, a proximal region and an inner surface defining a lumen extending therebetween. A stylet is disposed within the elongate sheath and has a distal region comprising a cutting surface, a proximal region and a lumen extending therebetween. The elongate sheath and the stylet include, in combination, an engagement section that is configured to limit relative axial movement between the elongate sheath and the stylet.

Another example embodiment of the invention can be found in an assembly that is configured for traversing a chronic total occlusion. The assembly includes an elongate shaft that has a distal region, a proximal region and a lumen extending therebetween. The assembly also includes a penetrating structure that is disposed within the elongate shaft lumen. The penetrating structure is held captive within the lumen such that relative axial movement between the elongate shaft and the penetrating structure is limited.

Another example embodiment of the invention can be found in a method of traversing a vascular occlusion. An apparatus including an elongate sheath and a stylet captively disposed within the elongate sheath is positioned such that a distal region of the apparatus is proximate an occlusion. The stylet is advanced distally such that a distal region of the stylet that includes a cutting surface extends distally beyond a distal region of the elongate sheath and contacts a surface of the occlusion. The stylet is moved such that its cutting surface contacts and penetrates the occlusion. Provision is also made for injecting contrast media to aid in visualizing the lesion.

BRIEF DESCRIPTION OF THE DRAWINGS

The invention may be more completely understood in consideration of the following detailed description of various embodiments of the invention in connection with the accompanying drawings, in which:

FIGS. 14-21 illustrate a particular use of the apparatus for penetrating a vascular occlusion.

DETAILED DESCRIPTION

Figure 1:
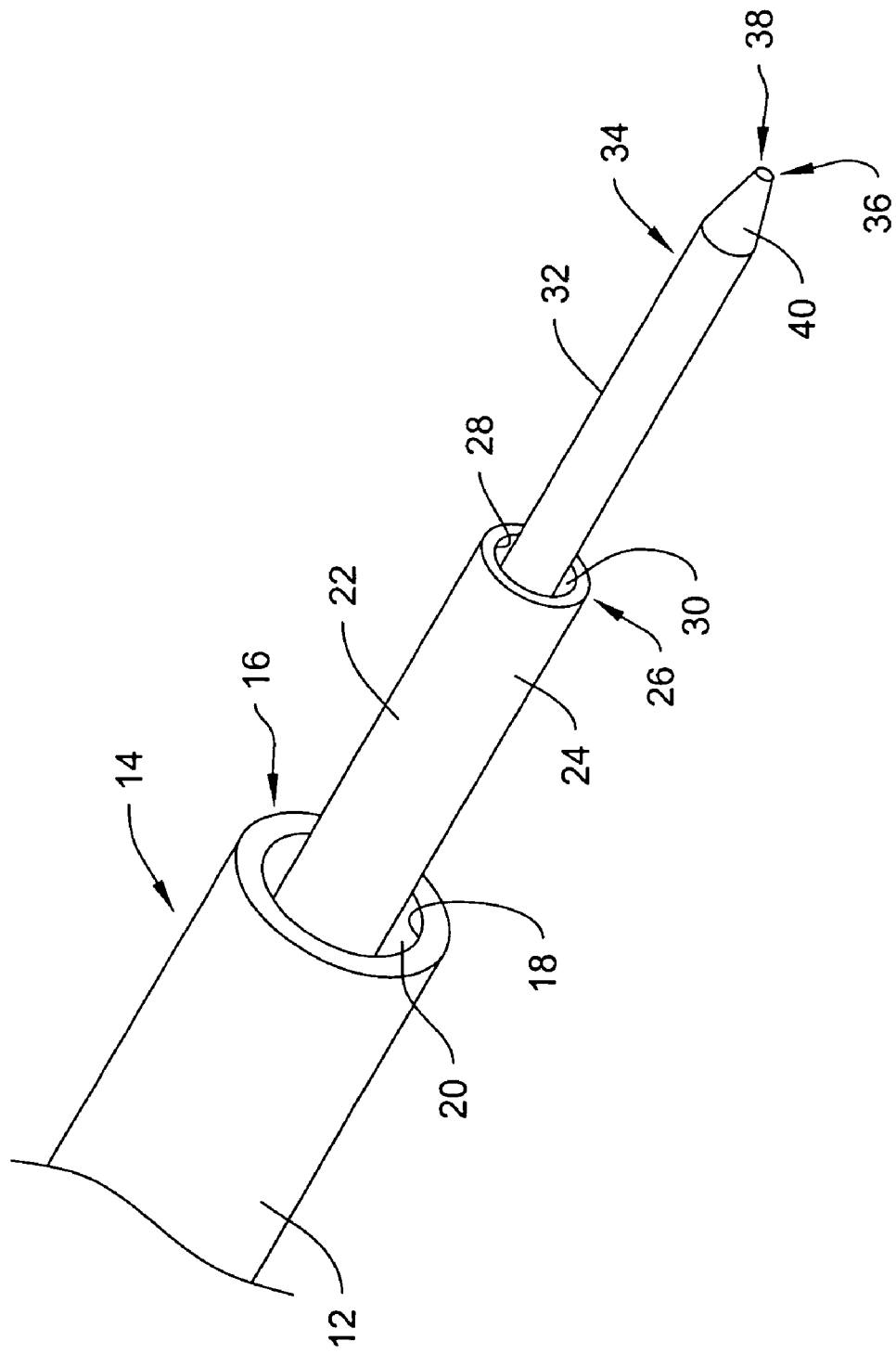
FIG. 1 is a perspective view of a recanalization apparatus for penetrating a vascular occlusion, in accordance with an embodiment of the invention.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

FIG. 1 is a perspective view of a recanalization assembly 10 in accordance with an embodiment of the present invention. The recanalization assembly 10 includes an elongate shaft 12 that has a distal region 14 defining a distal end 16. An inner surface 18 defines a shaft lumen 20. A sheath 22 is at least partially disposed within the shaft lumen 20. The sheath 22 includes a distal region 24 defining a distal end 26. An inner surface 28 defines a sheath lumen 30. A stylet 32 is at least partially disposed within the sheath lumen 30. The stylet 32 includes a distal region 34 defining a distal end 36. The distal end 36 includes an aperture 38 suitable to accommodate a guidewire as will be discussed in greater detail hereinafter. In the illustrated embodiment, the distal region 34 is defined at least in part by a needle tip 40 that can be configured for penetration into an occlusion.

In use, as will be discussed in greater detail hereinafter, the sheath 22 can be moved axially with respect to the elongate shaft 12. In some embodiments, the elongate shaft 12 can be advanced through a patient's vasculature before the sheath 22 has been deployed within the shaft lumen 20. Once the elongate shaft 12 has reached an appropriate position, the sheath 22 can be advanced distally through the shaft lumen 20. In other embodiments, the elongate shaft 12 can be advanced through the patient's vasculature with the sheath 22 already positioned within the shaft lumen 20.

The sheath 22 can be advanced distally so that its distal end 26 extends distally beyond the distal end 16 of the elongate shaft 12. The stylet 32 can move with respect to the sheath 22. In some embodiments, the stylet 32 can be moved axially such that its distal end 36 extends distally beyond the distal end 26 of the sheath 22. In some embodiments, the stylet 32 can undergo reciprocal motion so that the needle tip 40 can penetrate into an occlusion. In some embodiments, the stylet 32 can also rotate to aid in occlusion penetration. The stylet 32 can be made to move axially and/or rotationally using any known technique or method, both manual and mechanical means included.

Figure 2:
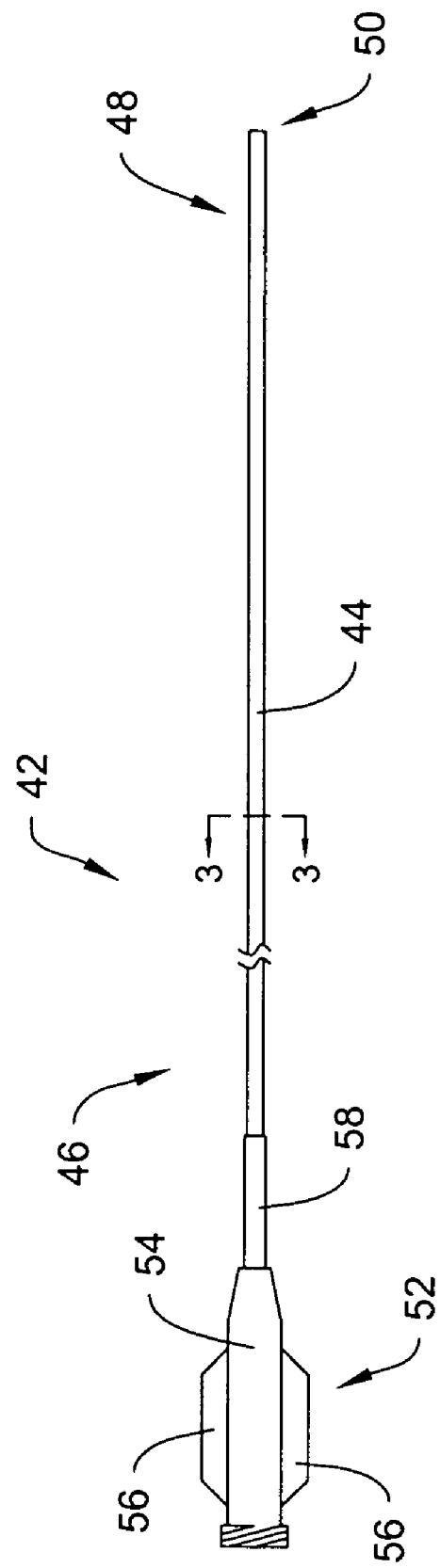
FIG. 2 is a plan view of a catheter in accordance with an embodiment of the invention.

FIG. 2 is a plan view of a catheter 42 in accordance with an embodiment of the invention. In some embodiments, the shaft 44 can be any of a variety of different catheters, but is preferably an intravascular catheter and will be discussed with respect to a catheter 42. Examples of intravascular catheters include balloon catheters, atherectomy catheters, drug delivery catheters, diagnostic catheters and guide catheters. Except as described herein, the catheter 42 can be manufactured using conventional techniques and materials.

The catheter 42 can be sized in accordance with its intended use. The catheter 42 can have a length that is in the range of about 50 centimeters to about 100 centimeters and can have a diameter that is in the range of about 4 F (French) to about 9 F.

In the illustrated embodiment, the catheter 42 includes an elongate shaft 44 that has a proximal region 46, a distal region 48 and a distal end 50. A hub and strain relief assembly 52 can be connected to the proximal region 46 of the elongate shaft 44. The hub and strain relief assembly 52 includes a main body portion 54, a pair of flanges 56 designed to improve gripping, and a strain relief 58 that is intended to reduce kinking. The hub and strain relief assembly 52 can be of conventional design and can be attached using conventional techniques.

Figure 3:
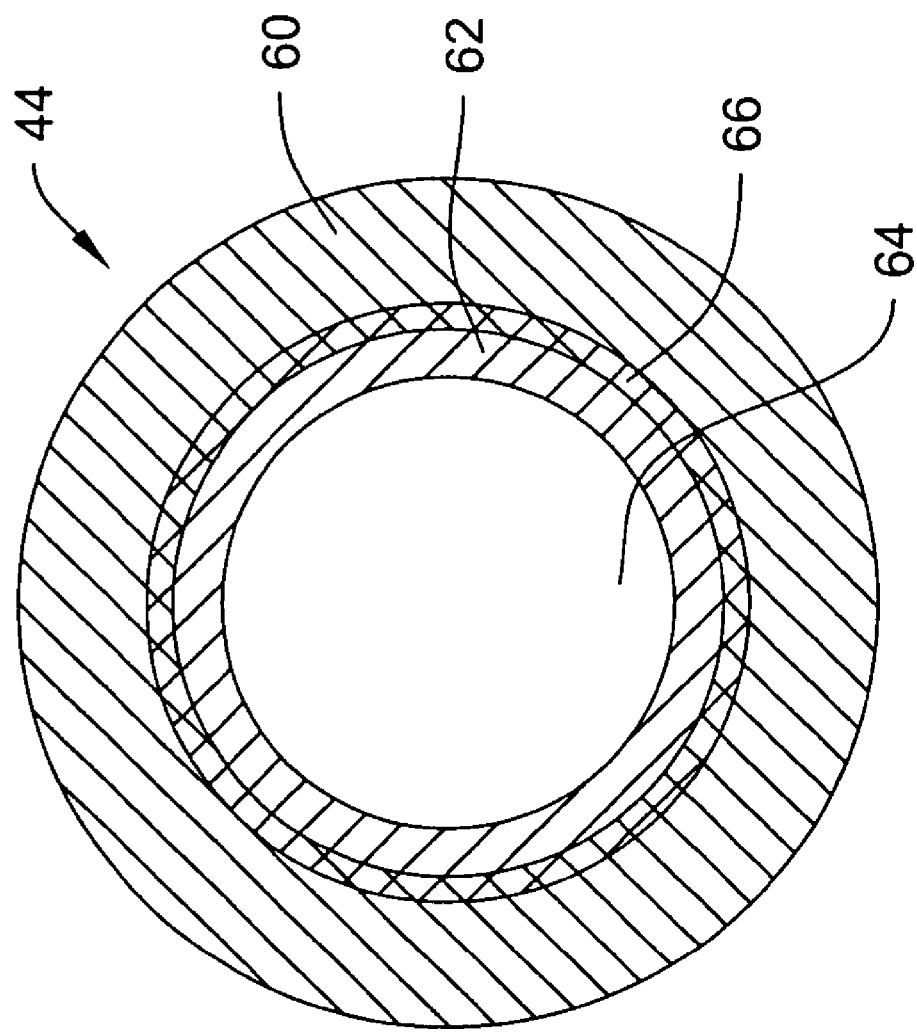
FIG. 3 is a cross-sectional view of the catheter of FIG. 1, taken along 3-3 line.

FIG. 3 is a cross-sectional view of one example of the elongate shaft 44, taken along line 3-3 of FIG. 2. The elongate shaft 44 includes an outer layer 60 and an inner layer 62. Each of the outer layer 60 and the inner layer 62 can extend from the proximal region 46 of the elongate shaft 44 to the distal region 48 of the elongate shaft 44. The inner layer 62 defines a lumen 64 that extends through the elongate shaft 44.

In some embodiments, the elongate shaft 44 can include a reinforcing braid or ribbon layer 66 to increase particular properties such as kink resistance. The reinforcing braid or ribbon layer 66 can be positioned between the outer layer 60 and the inner layer 62 and can provide adequate kink resistance without substantially increasing the overall profile of the elongate shaft 44. Alternatively, a single layer shaft can be utilized. An inflation lumen can also be provided, whether coaxial or in a multi-lumen co-extrusion, for example.

In some embodiments (not illustrated), the elongate shaft 44 can include one or more shaft segments having varying degrees of flexibility. For example, the elongate shaft 44 can include a proximal segment, an intermediate segment and a distal segment. In some embodiments, the elongate shaft 44 can also include a distal tip segment that can be formed from a softer, more flexible polymer. The elongate shaft 44 can include more than three segments, or the elongate shaft 44 can include fewer than three segments.

If the elongate shaft 44 has, for example, three segments such as a proximal segment, an intermediate segment and a distal segment, each segment can include an inner layer 62 that is the same for each segment and an outer layer that becomes increasingly more flexible with proximity to the distal end 50 of the elongate shaft 44. For example, the proximal segment can have an outer layer that is formed from a polymer having a hardness of 72 D (Durometer), the intermediate segment can have an outer layer that is formed from a polymer having a hardness of 68 D and the distal segment can be formed from a polymer having a hardness of 46 D.

If the elongate shaft 44 has three segments, each of the segments can be sized in accordance with the intended function of the resulting catheter 42. For example, the proximal segment can have a length of about 35 inches, the intermediate segment can have a length that is in the range of about 2 inches to about 3 inches, and the distal segment can have a length that is in the range of about 1 inch to about 1.25 inches.

The inner layer 62 can be a uniform material and can define a lumen 64 that can run the entire length of the elongate shaft 44 and that is in fluid communication with a lumen (not illustrated) extending through the hub assembly 52. The lumen 64 defined by the inner layer 62 can provide passage to a variety of different medical devices such as the sheath 22 (see FIG. 1), and thus the inner layer 62 can include, be formed from or coated with a lubricious material to reduce friction within the lumen 64. An exemplary material is polytetrafluoroethylene (PTFE), better known as TEFLON®. The inner layer 62 can be dimensioned to define a lumen 64 having an appropriate inner diameter to accommodate its intended use. In some embodiments, the inner layer 62 can define a lumen 64 having a diameter of about 0.040 inches to about 0.058 inches, and the inner layer 62 can have a wall thickness of about 0.001 inches.

The outer layer 60 can be formed from any suitable polymer that will provide the desired strength, flexibility or other desired characteristics. Polymers with low durometer or hardness can provide increased flexibility, while polymers with high durometer or hardness can provide increased stiffness. In some embodiments, the polymer material used is a thermoplastic polymer material. Some examples of some suitable materials include polyurethane, elastomeric polyamides, block polyamide/ethers (such as PEBAX®), silicones, and co-polymers. The outer layer 60 can be a single polymer, multiple layers, or a blend of polymers. By employing careful selection of materials and processing techniques, thermoplastic, solvent soluble, and thermosetting variants of these materials can be employed to achieve the desired results.

In particular embodiments, a thermoplastic polymer such as a co-polyester thermoplastic elastomer such as that available commercially under the ARNITEL® name can be used. The outer layer 60 can have an inner diameter that is about equal to the outer diameter of the inner layer 62.

In some embodiments, the outer layer 60 can have an inner diameter in the range of about 0.014 inches to about 0.060 inches and an outer diameter in the range of about 0.018 inches to about 0.0690 inches. Part or all of the outer layer 60 can include materials added to increase the radiopacity of the outer layer 60, such as 50% bismuth subcarbonate.

Figure 4:
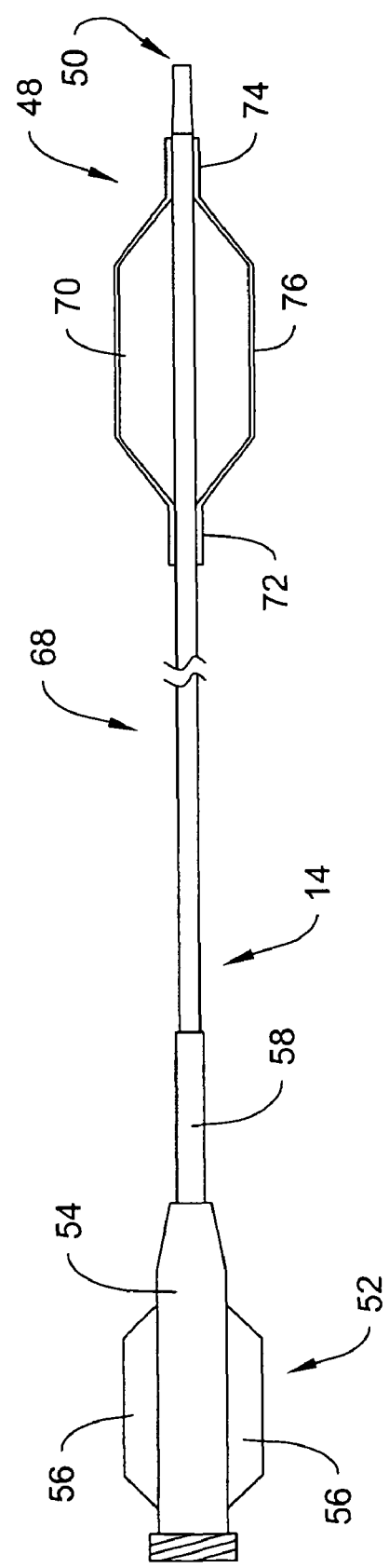
FIG. 4 is a plan view of a balloon catheter in accordance with an embodiment of the invention.

In particular embodiments, the catheter 44 can be a balloon catheter such as the balloon catheter 68 illustrated in FIG. 4. FIG. 4 is a plan view of a balloon catheter 68 that is similar in construction to the catheter 42, but includes a balloon 70 and an inflation lumen. As illustrated, the balloon 70 has a proximal waist 72, a distal waist 74 and an intermediate portion 76. The balloon 70 is seen in an expanded or inflated configuration. Construction of the balloon catheter 68 is conventional. Use of the balloon catheter 68 as the shaft 14 can have advantages that will be discussed in greater detail hereinafter.

Figure 5:
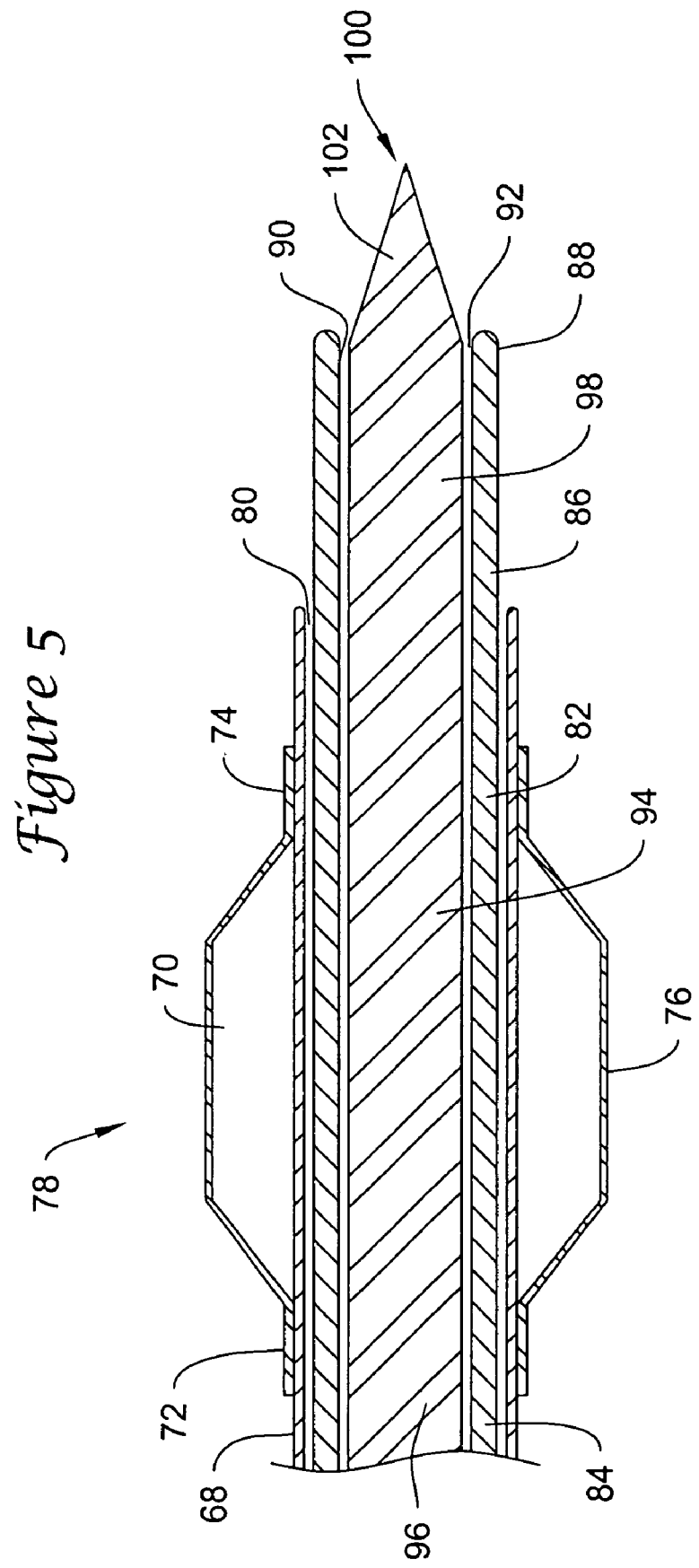
FIG. 5 is a partially sectioned view of the distal portion of a recanalization apparatus for penetrating a vascular occlusion, in accordance with an embodiment of the invention.

FIGS. 5 through 11 illustrate particular embodiments of recanalization assemblies employing a balloon catheter 68 (see FIG. 4) in accordance with the invention. Turning to FIG. 5, a distal portion of a recanalization assembly 78 is illustrated. The balloon catheter 68 defines a lumen 80 that is sized to accept an elongate sheath 82 that has a proximal region 84, a distal region 86 and a distal end 88. The lumen 80 can have an inner diameter that is in the range of about 0.014 to about 0.035 inches, which corresponds to typical guidewire dimensions.

The sheath 82 has an inner surface 90 defining a sheath lumen 92. The sheath 82 can be formed of any suitable polymeric material such as those discussed above with respect to the catheter 42 (see FIG. 2). The sheath 82 can also be formed of a suitable metallic material, such as nitinol, stainless steel, Elgiloy® and other alloys, that has been slit or otherwise processed to provide suitable flexibility and other desired characteristics. The sheath 82 can have an outer diameter of about 0.010 inches to about 0.035 inches, preferably about 0.014 inches to about 0.020 inches and an inner diameter of about 0.006 inches to about 0.030 inches, preferably about 0.008 inches to about 0.014 inches. The sheath 82 can have a length that is in the range of about 80 cm to about 150 cm, preferably about 135 cm.

A stylet 94 is disposed within the sheath lumen 92. The stylet 94 has a proximal region 96, a distal region 98 and a distal end 100. The distal region 98 can have an outer diameter that is in the range of about 0.004 to about 0.014 inches in order to minimize inadvertent tissue damage. The stylet 94 can have a length that is in the range of about 80 cm to about 150 cm. The distal region 98 includes a cutting surface 102 that as illustrated can be a needle tip. The stylet 94 can be formed of any suitable material. Exemplary materials include metals such as stainless steel, nitinol, Elgiloy®, titanium or other alloys. Although not shown in FIG. 5, the stylet can include a lumen therethrough in some preferred embodiments, as shown in FIG. 1. The lumen allows passage of a guidewire after the occlusion is penetrated.

As can be seen, the stylet 94 can be moved axially within the sheath 82, and the sheath 82 can be moved axially within the balloon catheter 68. In other embodiments, the recanalization assembly 78 can include structure that limits relative axial travel between the sheath 82 and the stylet 94. The stylet in FIGS. 5-11 can pierce the proximal or distal cap of the occlusion via application of a forward pushing force, alone or in combination with a turning action imparted to the stylet. The turning action can be applied to the stylet as shown in FIG. 1 by digital manipulation or mechanical means (not shown). These embodiments are shown, for example, in FIGS. 6-11.

Figure 6:
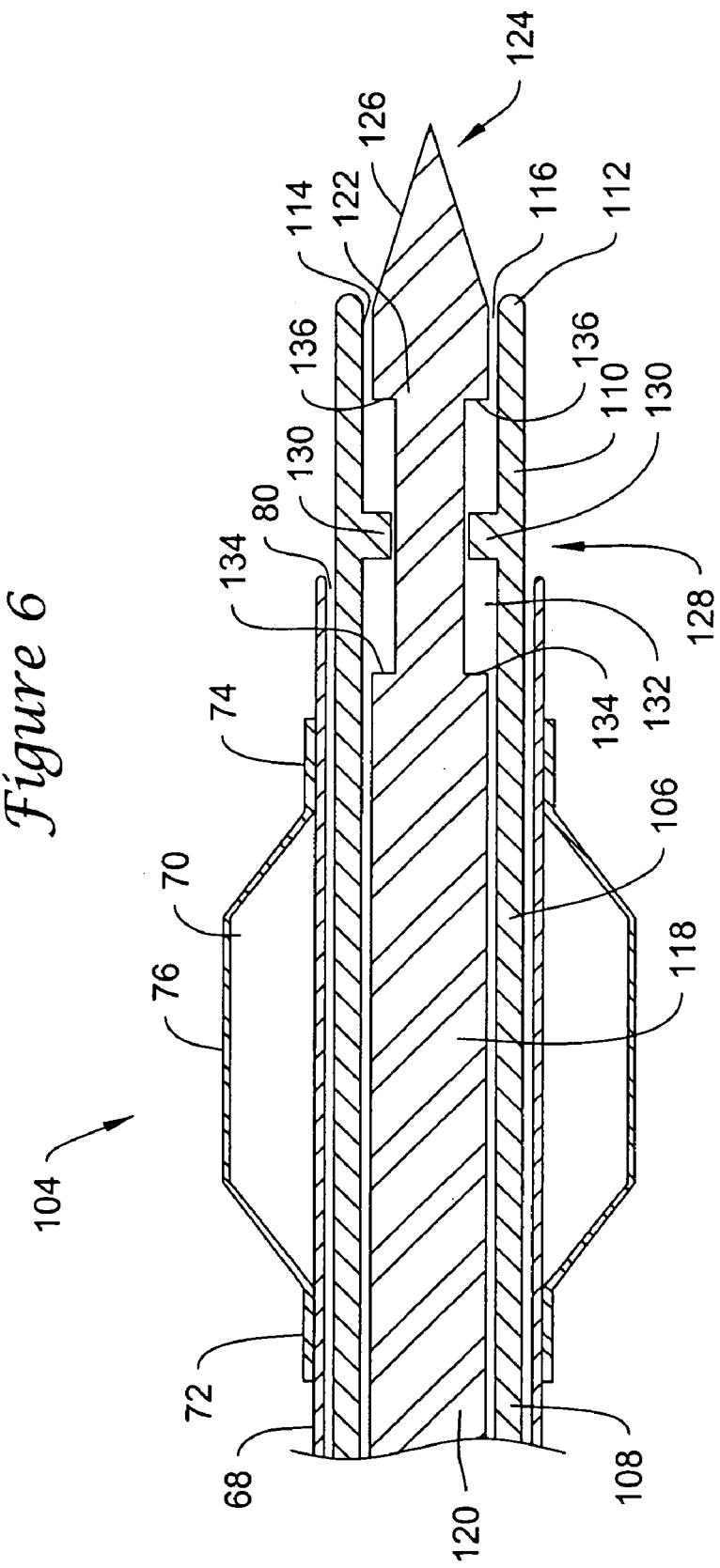
FIG. 6 is a partially sectioned view of the distal portion of a recanalization apparatus for penetrating a vascular occlusion, in accordance with an embodiment of the invention.

Turning now to FIG. 6, a recanalization assembly 104 is illustrated as including the balloon catheter 68. A sheath 106 having a proximal region 108, a distal region 110 and a distal end 112 is disposed within the lumen 80. The sheath 106 includes an inner surface 114 defining a sheath lumen 116. A stylet 118 having a proximal region 120, a distal region 122 and a distal end 124 is disposed within the sheath lumen 116. The distal region 122 can define a cutting surface 126. The sheath 106 and the stylet 118 can be formed of any suitable materials and have any suitable dimensions as discussed with respect to FIG. 5.

The recanalization assembly 104 includes an engagement section 128 that is configured to limit relative axial movement between the sheath 106 and the stylet 118. The engagement section 128 can be positioned anywhere along the sheath 106 and the stylet 118. In some embodiments, as illustrated, the engagement section 128 can be positioned proximate the distal region of the sheath 106 and the stylet 118 for greater control and accuracy.

In the illustrated embodiment, the sheath 106 includes a stop 130 that can be a cylindrical stop having an inner diameter that is less than an inner diameter of the sheath 106 on either side of the stop 130. The stop 130 can be integrally formed with the sheath 106 or can be independently formed and subsequently secured using any suitable technique. In some embodiments, the stop 130 can continue for an entire circumference (360 degrees) of the sheath 106. In other embodiments, the stop 130 can include one or more distinct sections spaced apart along the circumference of the sheath 106.

The stylet 118 includes an engagement portion 132 that has a proximal end 134 and a distal end 136. The engagement portion 132 can have an outer diameter that is reduced with respect to an outer diameter of the stylet 118 on either side of the engagement portion 132. As can be seen, distal movement of the stylet 118 is limited by the stop 130 contacting the proximal end 134 of the engagement portion 132. Similarly, proximal movement of the stylet 118 is limited by the stop 130 contacting the distal end 136 of the engagement portion.

In some embodiments, the stylet 118 can be withdrawn proximally such that the cutting surface 126 is completely within the sheath lumen 116. This permits extending the sheath 106 distally through the balloon catheter lumen 80 without contacting the vasculature distal of the balloon catheter 68. In some embodiments, the distal end 124 of the stylet 118 can extend beyond the distal end 112 of the sheath 106 even when withdrawn.

Figure 7:
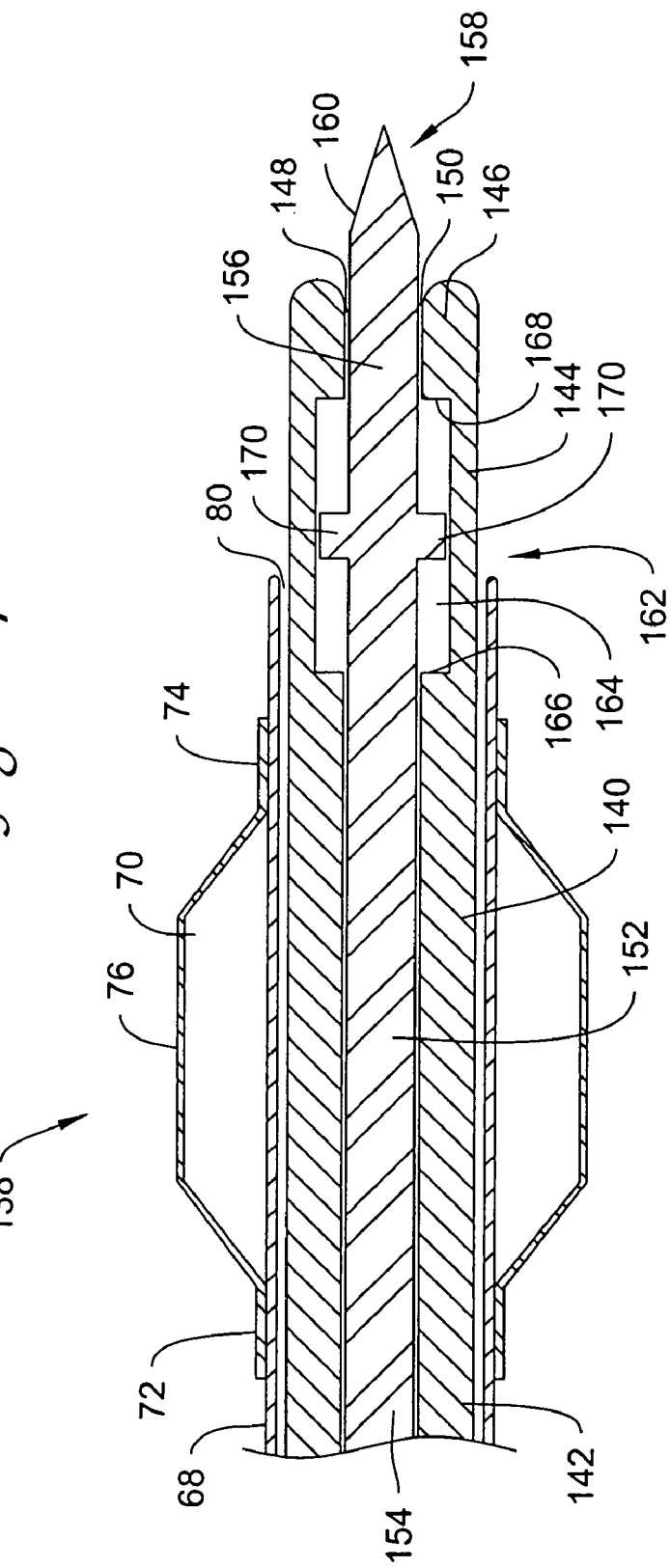
FIG. 7 is a partially sectioned view of the distal portion of a recanalization apparatus for penetrating a vascular occlusion, in accordance with an embodiment of the invention.

Turning now to FIG. 7, a recanalization assembly 138 is illustrated as once again including the balloon catheter 68. A sheath 140 having a proximal region 142, a distal region 144 and a distal end 146 is disposed within balloon catheter lumen 80. The sheath 140 includes an inner surface 148 that defines a sheath lumen 150. A stylet 152 having a proximal region 154, a distal region 156 and a distal end 158 is disposed within the sheath lumen 150. The distal region 158 includes a cutting surface 160 that can in some embodiments be a needle tip. The sheath 140 and the stylet 152 can be formed of any suitable materials and have any suitable dimensions as discussed with respect to FIG. 5. As with prior embodiments, the stylet 152 can include a lumen therethrough (now shown) for passage of a guidewire.

The recanalization assembly 138 includes an engagement section 162 that is configured to limit relative axial movement between the sheath 140 and the stylet 152. The sheath 140 includes an engagement portion 164 having a proximal end 166 and a distal end 168. The engagement portion 164 has an inner diameter that is greater than an inner diameter of the sheath 140 on either side of the engagement portion 164. The engagement portion 164 can be integrally formed with the sheath 140, or the sheath 140 can be formed and material can subsequently be removed using any suitable technique to form the increased inner diameter engagement portion 164.

The engagement section 162 also refers to a portion of the stylet 152. The stylet 152 includes a stop 170 that has an outer diameter that is greater than an outer diameter of the stylet 152 on either side of the stop 170. In some embodiments, the stop 170 can continue for an entire circumference (360 degrees) of the stylet 152. In other embodiments, the stop 170 can include one or more distinct sections spaced apart along the circumference of the stylet 152. As can be seen, proximal movement of the stylet 152 is limited by the stop 170 contacting the proximal end 166 of the engagement portion 164. Similarly, distal movement of the stylet 152 is limited by the stop 170 contacting the distal end 168 of the engagement portion 164.

In some embodiments, the distal end 158 of the stylet 152 can remain proximal of the distal end 146 of the sheath 140, while in other embodiments, the distal end 158 of the stylet 152 can extend distally beyond the distal end 146 of the sheath 140 when the stylet 152 is completely retracted.

In comparing FIG. 6 to FIG. 7, it is clear that the stylet 152 of FIG. 7 is narrower than the stylet 118 of FIG. 6. In some embodiments, a thinner stylet can be advantageous as this can provide for additional flexibility. In other embodiments, a stronger or stiffer stylet can permit application of additional force in attempting to break through an occlusion. The sheath 140 of FIG. 7 has thicker walls than the sheath 106 of FIG. 6.

In some embodiments, a thicker-walled sheath can be advantageous as this can provide for additional pushability. In other embodiments, a thinner-walled sheath may be more flexible.

Figure 8:
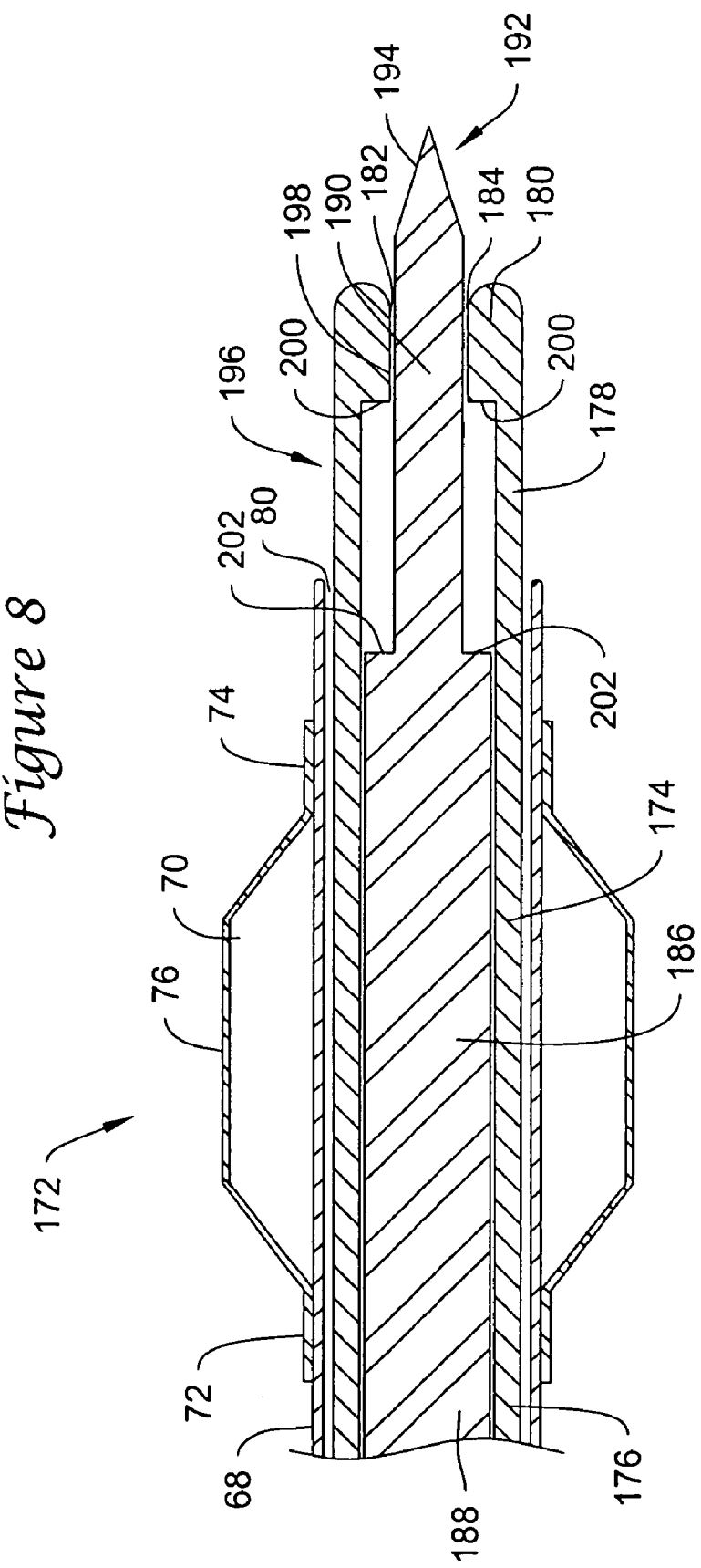
FIG. 8 is a partially sectioned view of the distal portion of a recanalization apparatus for penetrating a vascular occlusion, in accordance with an embodiment of the invention.

Turning now to FIG. 8, a recanalization assembly 172 is illustrated as including the balloon catheter 68. A sheath 174 having a proximal region 176, a distal region 178 and a distal end 180 is disposed within balloon catheter lumen 80. The sheath 174 includes an inner surface 182 that defines a sheath lumen 184. A stylet 186 having a proximal region 188, a distal region 190 and a distal end 192 is disposed within the sheath lumen 184. The distal region 190 includes a cutting surface 194 that can in some embodiments be a needle tip. The sheath 174 and the stylet 186 can be formed of any suitable materials and have any suitable dimensions as discussed with respect to FIG. 5. Further, the stylet can include a lumen therethrough for guidewire passage.

The recanalization assembly 172 includes an engagement section 196 that is configured to limit distal travel of the stylet 186 with respect to the sheath 174. The sheath 174 includes an engagement portion 198 having an inner diameter that is reduced with respect to an inner diameter of the sheath 174 proximal of the engagement portion 198. The engagement portion 198 terminates at a distal stop 200.

The engagement section 196 also pertains to the distal region 190 of the stylet 186, which terminates at a proximal stop 200. The distal region 190 has a reduced outer diameter with respect to an outer diameter of the stylet 186 proximal of the engagement section 196. As can be seen, distal travel of the stylet 186 is limited by the proximal stop 202 of the stylet 186 contacting the distal stop 200 of the sheath 174. In this embodiment, the stylet 186 can be completely removed proximally from the sheath 174, should there be a need to inject contrast fluid or deploy a different device.

In some embodiments, the distal end 192 of the stylet 186 can remain proximal of the distal end 180 of the sheath 174, while in other embodiments the distal end 192 of the stylet 186 can extend distally beyond the distal end 180 of the sheath 174 when the stylet 186 is completely retracted.

Figure 9:
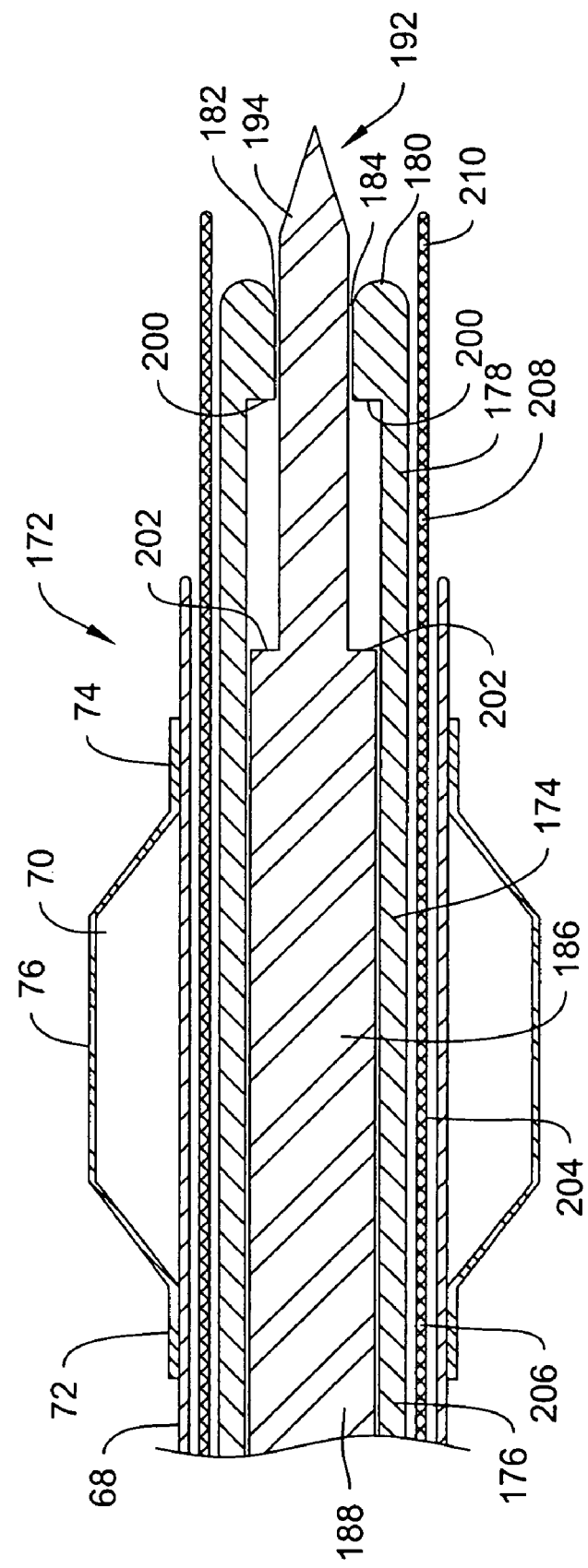
FIG. 9 is a partially sectioned view of the distal portion of a recanalization apparatus for penetrating a vascular occlusion, in accordance with an embodiment of the invention.

In some embodiments, such as illustrated in FIG. 9, a second sheath 204 can be deployed inside the balloon catheter lumen 80 but exterior to the sheath 174. The second sheath 204 has a proximal region 206, a distal region 208 and a distal end 210. The second sheath 204 can be used in situations in which the sheath 174 has an outer diameter that is somewhat less than an inner diameter of the balloon catheter lumen 80 in order to reduce the size differential between the balloon catheter 68 and the sheath 174 and to provide for easier exchange for other devices. The second sheath 204 can extend across the opening in the distal cap and hold in position to allow the sheath and stylet to be exchanged for a guidewire. In some embodiments, the second sheath 204 can have an inner diameter that is about 0.010 to about 0.014 inches and an outer diameter that is about 0.014 to about 0.018 inches in order to account for standard guidewire sizes. The second sheath 204 can be formed of any suitable material as discussed with respect to the catheter 42 (see FIG. 2).

In some embodiments, the second sheath 204 can be employed in order to move the sheath 174 and the stylet 186 distally further from the balloon 76. While FIG. 9 shows the second sheath 204 deployed with the recanalization assembly 172 illustrated in FIG. 8, it is important to note that the second sheath 204 can also be used with the embodiments illustrated in the previous Figures.

Figure 10:
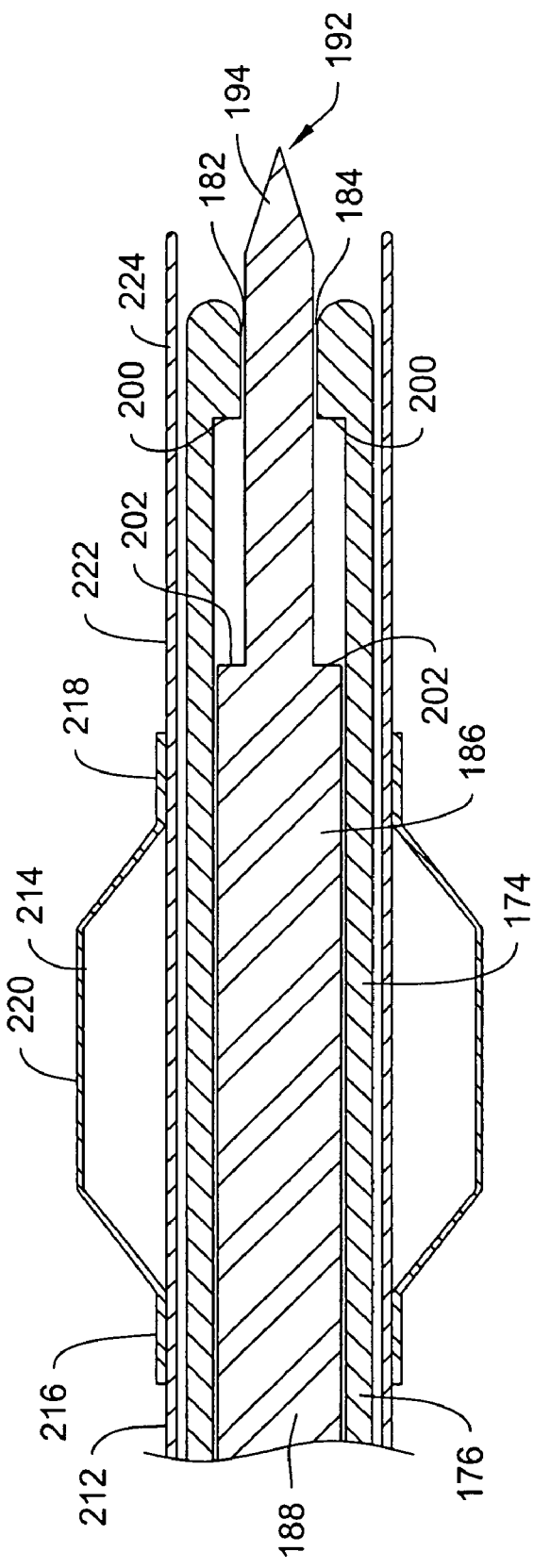
FIG. 10 is a partially sectioned view of the distal portion of a recanalization apparatus for penetrating a vascular occlusion, in accordance with an embodiment of the invention.

In a similar embodiment, shown in FIG. 10, recanalization assembly 172 includes a balloon catheter 212 having a balloon 214. The balloon 214 has a proximal waist 216, a distal waist 218 and an intermediate portion 220. The balloon catheter 212 differs from the balloon catheter 68 previously described herein by virtue of having a shaft 222 that extends distally beyond the balloon 214. The shaft 222 includes a distal region 224 that can function to allow the shaft 222 to extend across the opening that is made in the proximal cap and then allow the shaft and stylet to be withdrawn and replaced by a guidewire suitable for extending further through the occlusion. While FIG. 10 shows the elongated balloon catheter shaft 222 deployed with the recanalization assembly 172, it is important to note that the elongated balloon catheter shaft 222 can be used with the embodiments illustrated in the previous Figures.

Figure 11:
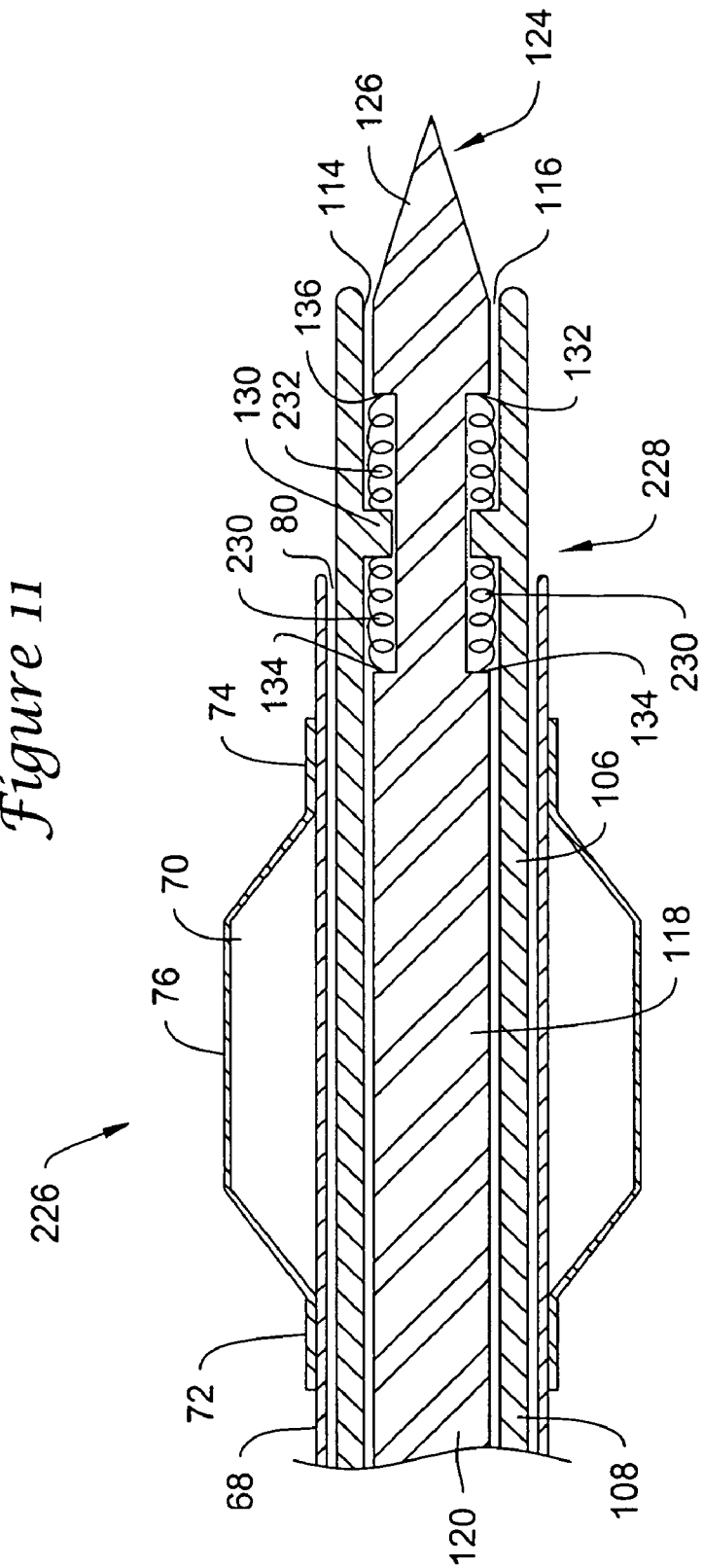
FIG. 11 is a partially sectioned view of the distal portion of a recanalization apparatus for penetrating a vascular occlusion, in accordance with an embodiment of the invention.

FIG. 11 shows another embodiment related to that of FIG. 6. FIG. 11 illustrates a recanalization assembly 226 deployed within the balloon catheter 68 previous described. In this embodiment, however, the engagement section 228 includes biasing structure that can be used to forcibly move the stylet 118 distally with respect to the sheath 106. Any suitable biasing structure, such as a resilient material or spring, can be used.

In the illustrated embodiment, the biasing structure includes one or more proximal springs 230 that are positioned between the stop 130 and the proximal end 134 of the engagement portion 132 and one or more distal springs 232 that are positioned between the stop 130 and the distal end 136 of the engagement portion 132. In some embodiments, the biasing structure can include only the proximal springs 230, with the distal springs 232 being absent. In other embodiments, the biasing structure can include only the distal springs 232, with the proximal springs 230 being absent.

In use, the stylet 118 can be moved proximally. In the illustrated embodiment, moving the stylet 118 proximally can compress the proximal springs 230 from their equilibrium length with extending the distal springs 232 from their equilibrium length. Letting go of the stylet 118 will permit the proximal springs 230 and the distal springs 232 to release the potential energy stored therein as a result of their displacement from their equilibrium lengths. As a result, the stylet 118 can be driven forcibly in a distal direction such that the cutting surface 126 can contact and penetrate an occlusion.

Figure 12:
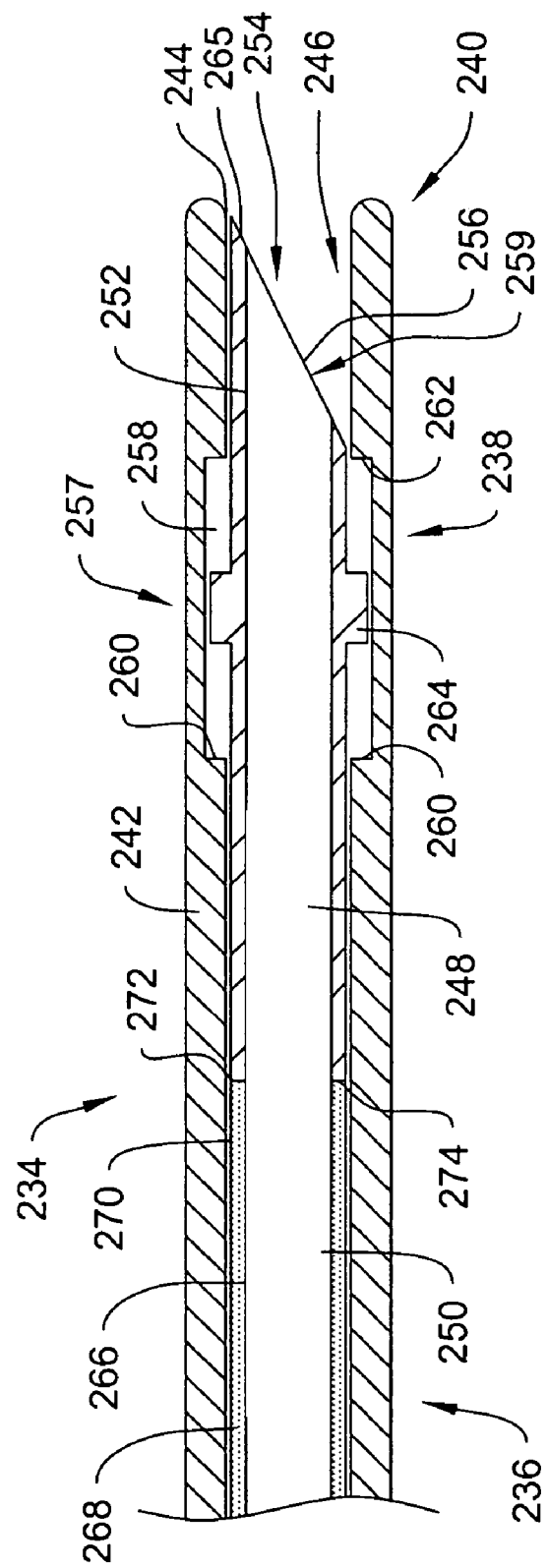
FIG. 12 is a partially sectioned view of the distal portion of an apparatus for penetrating a vascular occlusion, in accordance with an embodiment of the invention.
Figure 13:
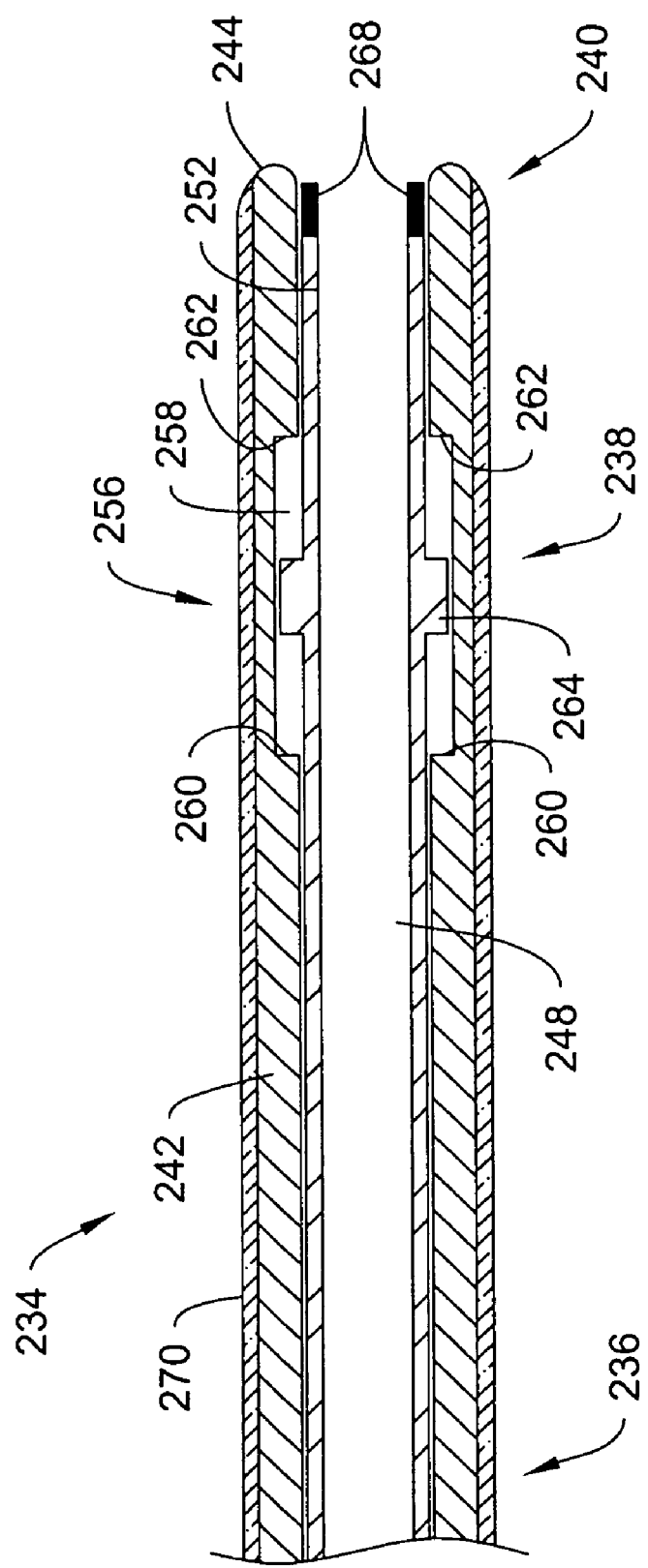
FIG. 13 is a partially sectioned view of the distal portion of an apparatus for penetrating a vascular occlusion, in accordance with an embodiment of the invention.

FIGS. 12 and 13 illustrate other embodiments of the invention that employ a piercing catheter. In particular, FIG. 12 shows a piercing catheter 234 having a proximal region 236, a distal region 238 and a distal end 240. The piercing catheter 234 includes an elongate shaft 242 that has an inner surface 244 defining a shaft lumen 246. A stylet 248 is disposed within the shaft lumen 246. The stylet 248 has a proximal region 250, a distal region 252 and a distal end 254. The stylet 248 has a stylet lumen 259 that extends from the proximal region 250 through the distal region 252. The distal region 252 of the stylet 248 includes an angled cutting needle surface 254.

The piercing catheter 234 can be formed of any suitable materials such as those discussed above with respect to the catheter 42 (see FIG. 2). Exemplary materials for forming the shaft 242 include nylon, PEBAX®, polyethylene, polyurethane and copolymers thereof. Further, the shaft can be metallic, with or without slots. The shaft 242 can have a length that is in the range of about 80 cm to about 150 cm. The shaft 242 can have an outer diameter that is in the range of about 0.012 inches to about 0.035 inches and an inner diameter that is in the range of about 0.008 inches to about 0.030 inches. The stylet 248 can be formed of any suitable material including stainless steel, nitinol, Elgiloy®, other alloys or polymers and can have a length that is in the range of about 80 cm to about 150 cm, an outer diameter that is in the range of about 0.007 inches to about 0.031 inches and an inner diameter that is in the range of about 0.005 inches to about 0.027 inches.

The piercing catheter 234 includes an engagement section 257 that is configured to limit relative axial movement between the elongate shaft 242 and the stylet 248. The inner surface 244 of the elongate shaft 242 includes an engagement portion 258 that has an inner diameter that is less than an inner diameter of the elongate shaft 242 on either side of the engagement portion 258. The engagement portion 258 has a proximal end 260 and a distal end 262. The engagement portion 258 can have a length between the proximal end 260 and the distal end 262 that is in the range of about 2 mm to about 10 mm, preferably about 3 mm to about 6 mm.

The engagement section 257 also pertains to the stylet 248. The stylet 248 has a stop 264 that has a larger outer diameter than an outer diameter of the stylet 248 on either side of the stop 264. In some embodiments, the stop 264 can be a cylindrical stop that extends circumferentially all the way around the stylet 248 while in other embodiments the stop 264 can include one or more distinct sections that are circumferentially spaced around the stylet 248. As can be seen, proximal travel of the stylet 248 is limited by the stop 264 contacting the proximal end 260 of the engagement portion 258 while distal travel of the stylet 248 is limited by the stop 264 contacting the distal end 262 of the engagement portion 258.

In some embodiments, the stylet 248 can extend proximally through the elongate shaft 242. In other embodiments, as illustrated, the stylet 248 can be shorter than the elongate shaft 242. A pushing tube 266 can have a proximal region 268, a distal region 270 and a distal end 272. The distal end 272 of the pushing tube 266 can contact a proximal end 274 of the stylet 248. In some embodiments, there may be advantages in having a shortened stylet 248 disposed in the distal region 238 of the piercing catheter 234 while a pushing tube 266 having different strength and flexibility characteristics is disposed proximally thereof. The stylet lumen 259 can, in some embodiments, allow for passage of a guidewire through the surface 254 after the stylet 248 has crossed the proximal cap. The angled cutting surface 254 allows the stylet 248 to be rotated within the sheath and allows the tip 265 of the stylet to be centered on the proximal cap via fluoroscopic imaging techniques.

FIG. 13 shows a similar embodiment in which the distal region 252 of the stylet 248 includes a cylindrical cutting edge 268 rather than the angled cutting needle surface 256 shown in FIG. 12. FIG. 13 shows a stylet 248 that extends proximally and thus inclusion of a pushing tube 266 is not necessary. The embodiment shown in FIG. 13 also adds an optional second sheath 270 to the piercing catheter 234 to function similar to the second sheath 204 shown in FIG. 9. The stylet 248 can be rotated to assist in crossing the proximal cap.

Figure 14:
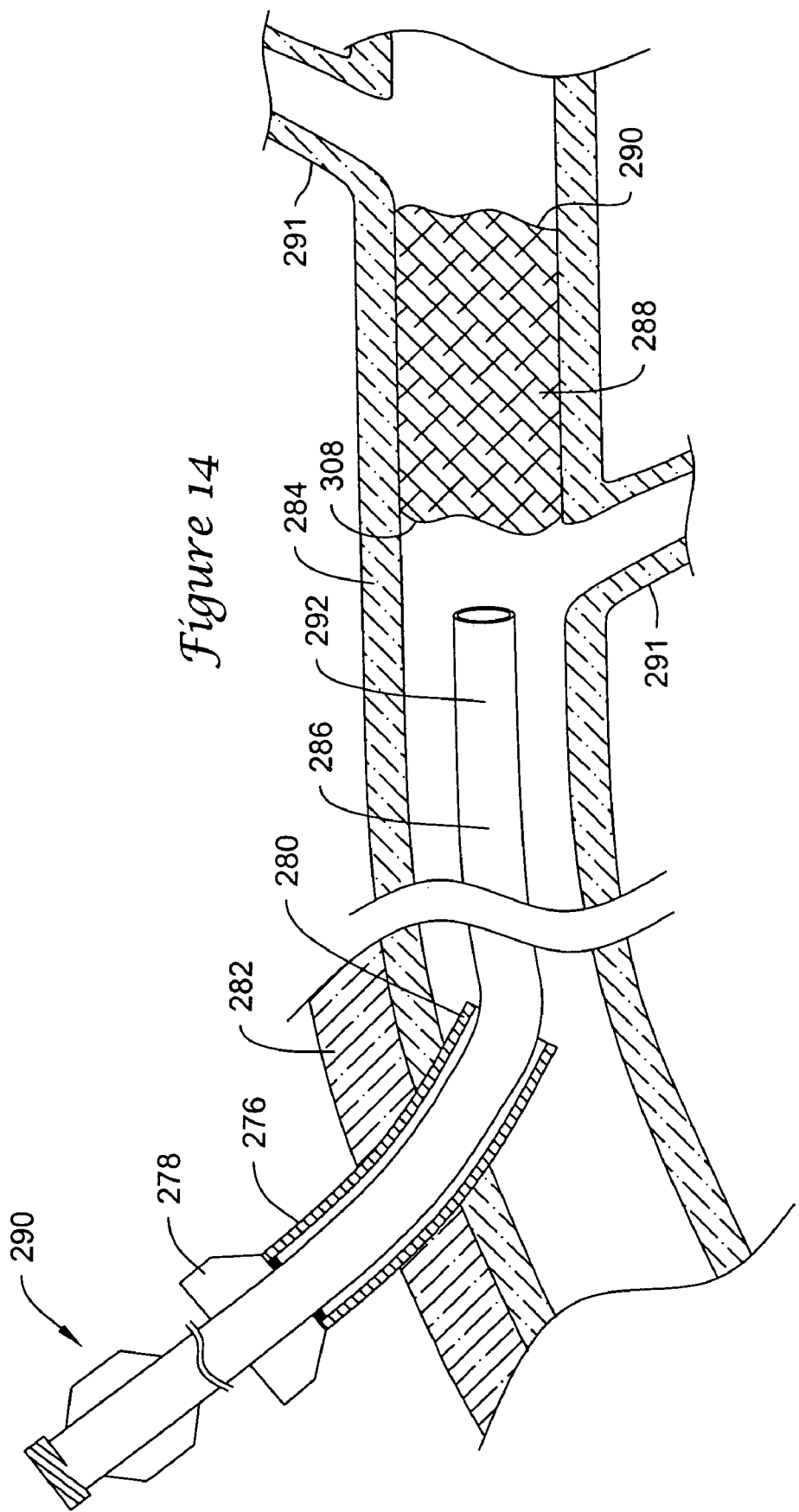

FIGS. 14 through 17 illustrate a possible use of the recanalization assemblies described herein. In FIG. 14, an introducer sheath 276 having a proximal region 278 and a distal region 280 has been introduced through a patient's tissue 282 into the patient's vasculature 284 as is well known in the art. A catheter 286 that in some embodiments can be a balloon catheter has been inserted into the proximal region 278 of the introducer sheath 276 and has been advanced to a position near a desired treatment site, such as an occlusion 288 having a proximal cap 308, distal cap 290 and side branch 291. The catheter 286 has a proximal region 290 and a distal region 292.

Figure 15:
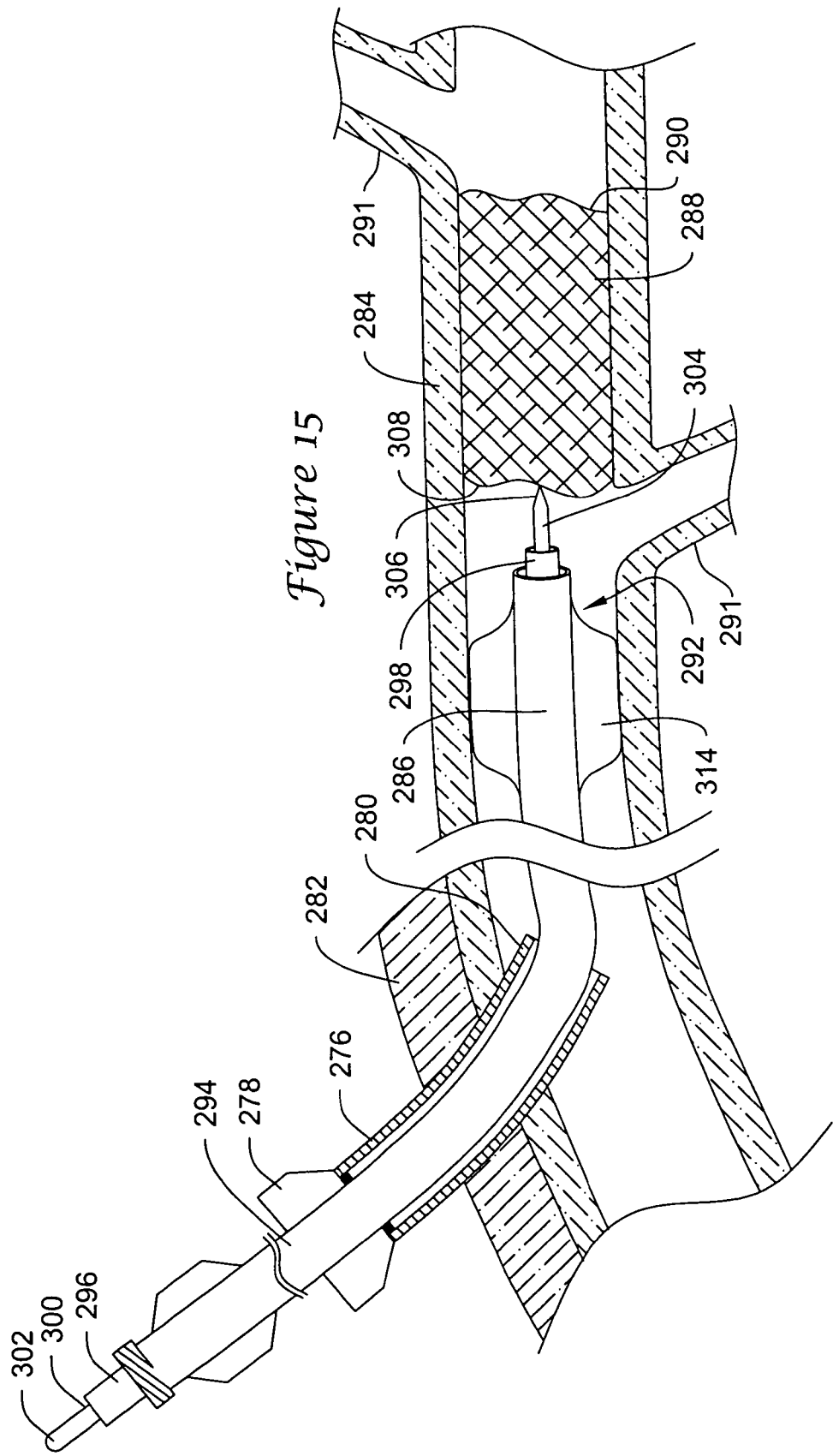

Turning now to FIG. 15, a sheath 294 having a proximal region 296 and a distal region 298 can be deployed within the catheter 286. The catheter 286 includes a balloon 314 that can be inflated prior to deploying the sheath 294. The balloon can be a dilating balloon or a gentle elastomeric centering balloon made from, for example, latex or polyurethane. In some embodiments, there may be advantages in deploying the sheath 294 prior to inflating the balloon 314. The balloon 314, once inflated, can aid in centering the sheath 294 and thus can assist the sheath 294 and enclosed stylet 300 in properly contacting the occlusion 288 without damaging the vessel wall. The stylet 300 has a proximal region 302 and a distal region 304. The distal region 304 includes a needle tip 306 that is positioned (as illustrated) proximate the occlusion 288.

Figure 16:
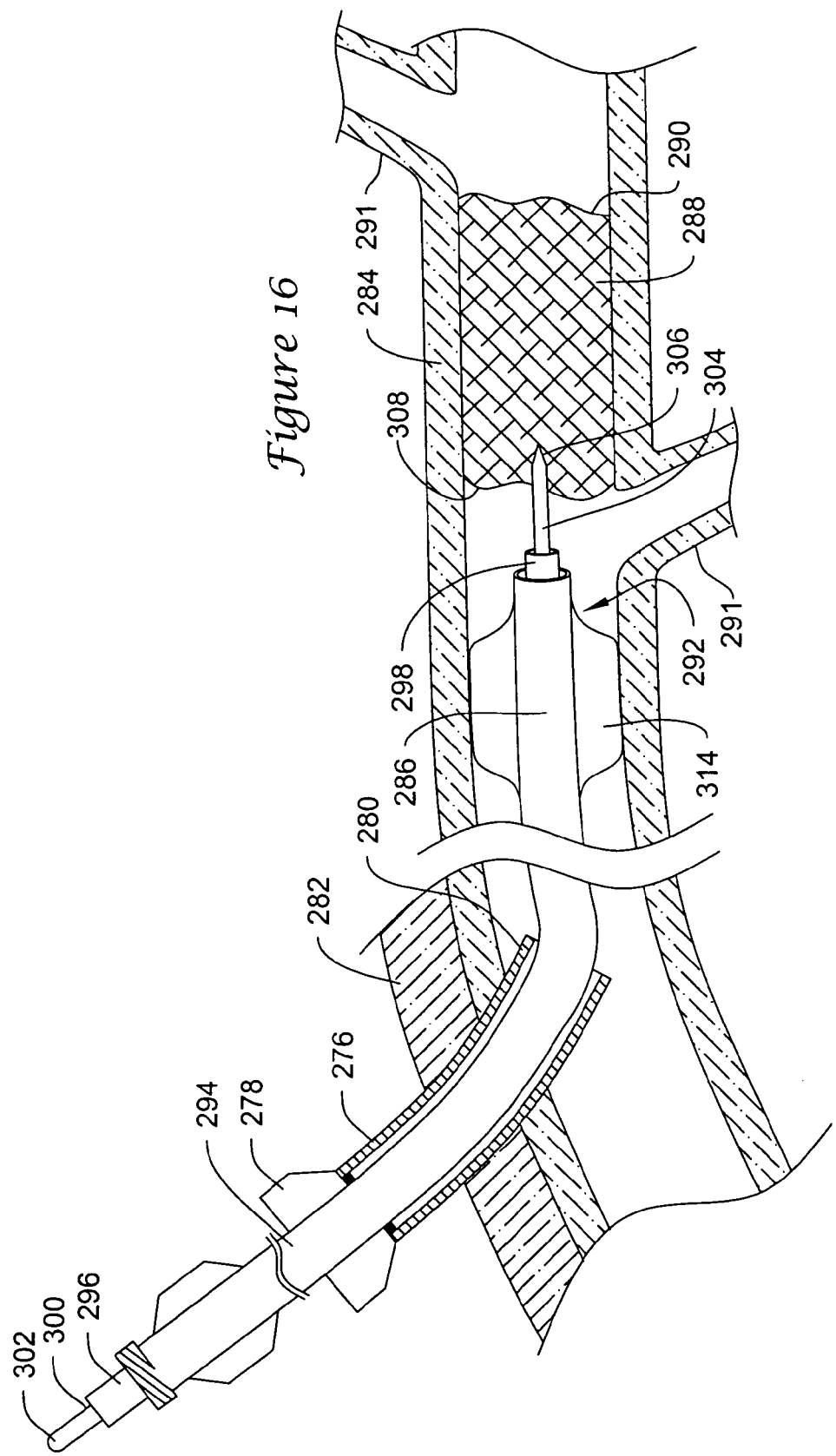
Figure 17:
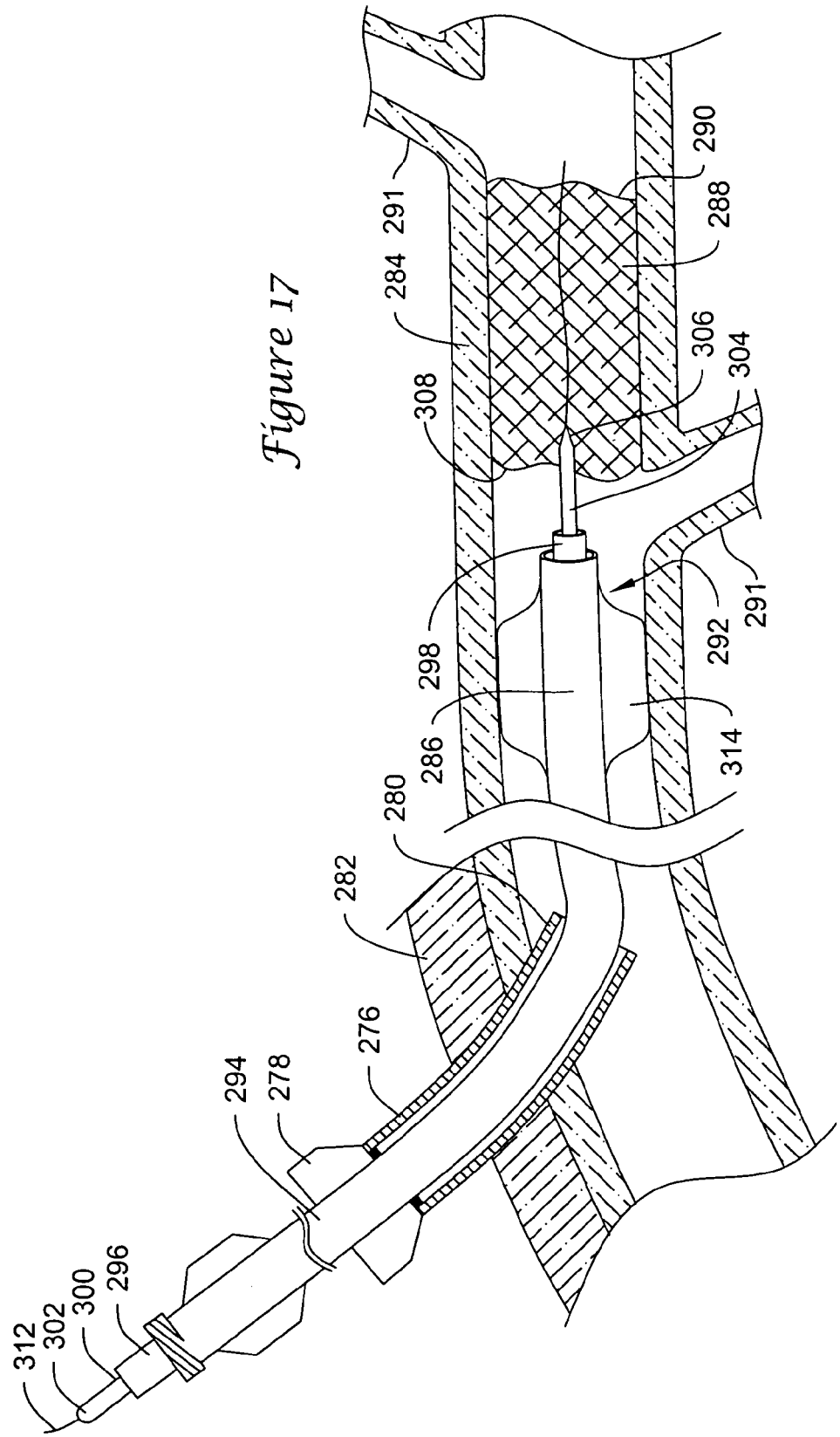
Figure 18:
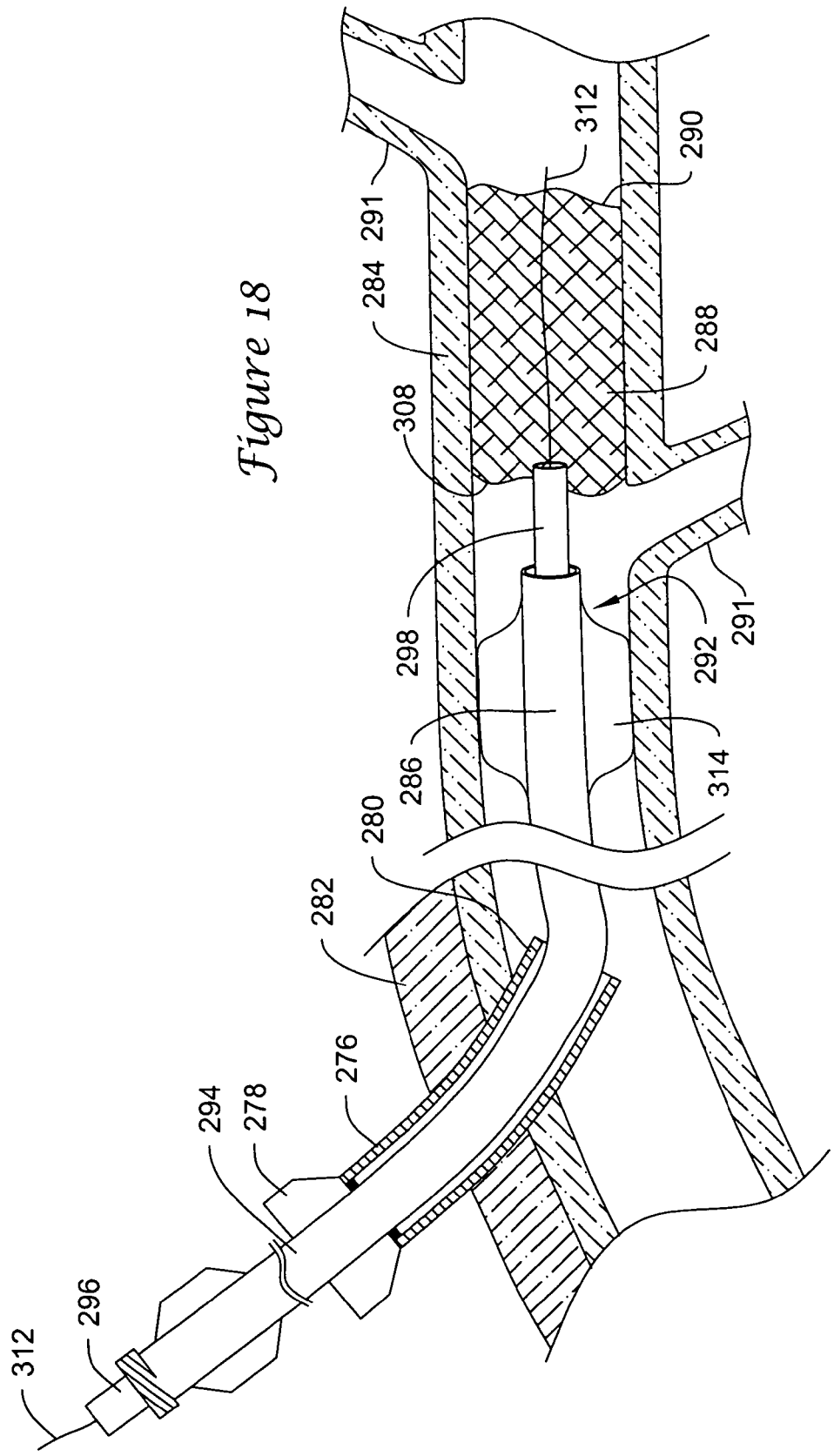
Figure 19:
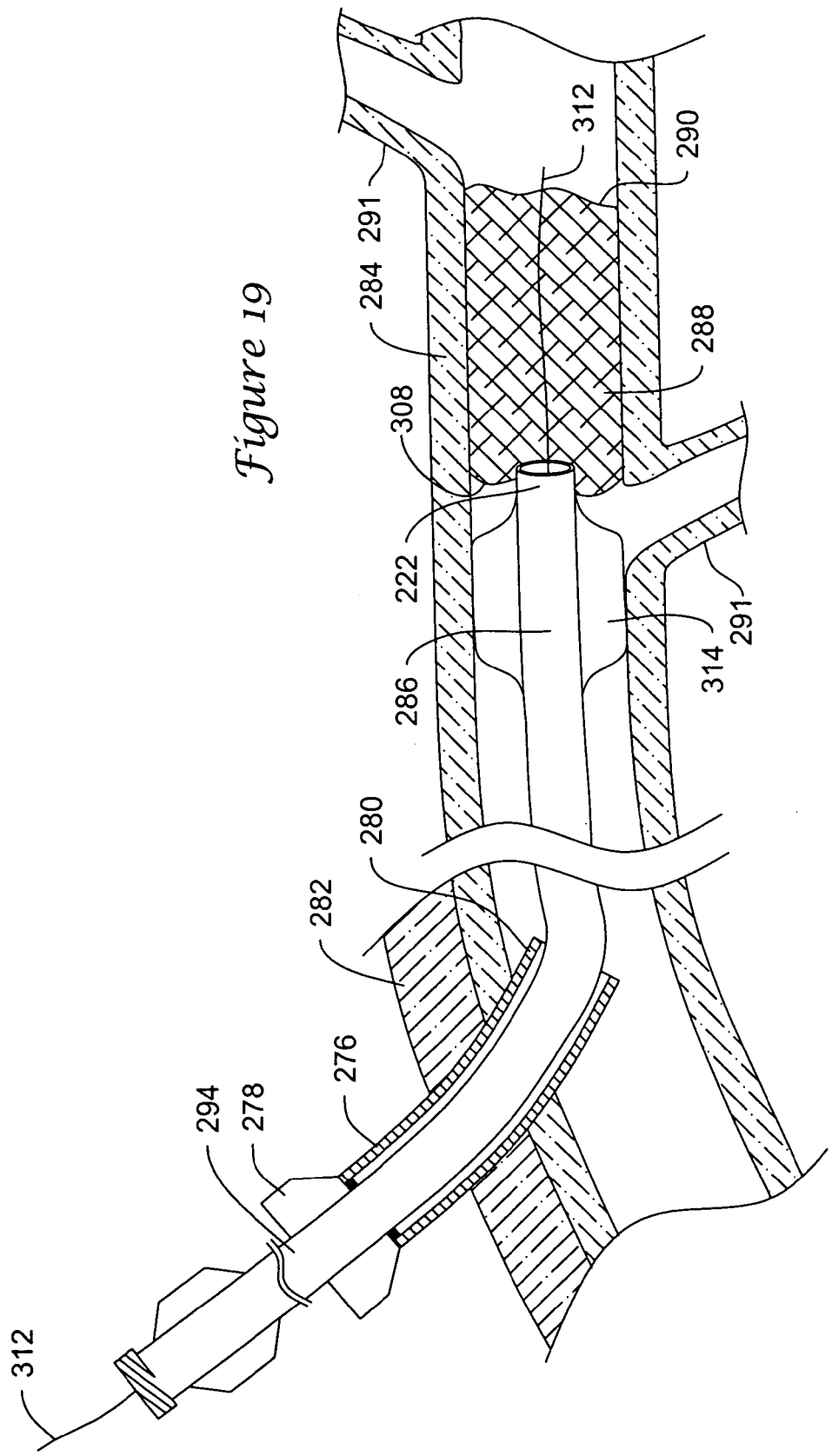
Figure 20:
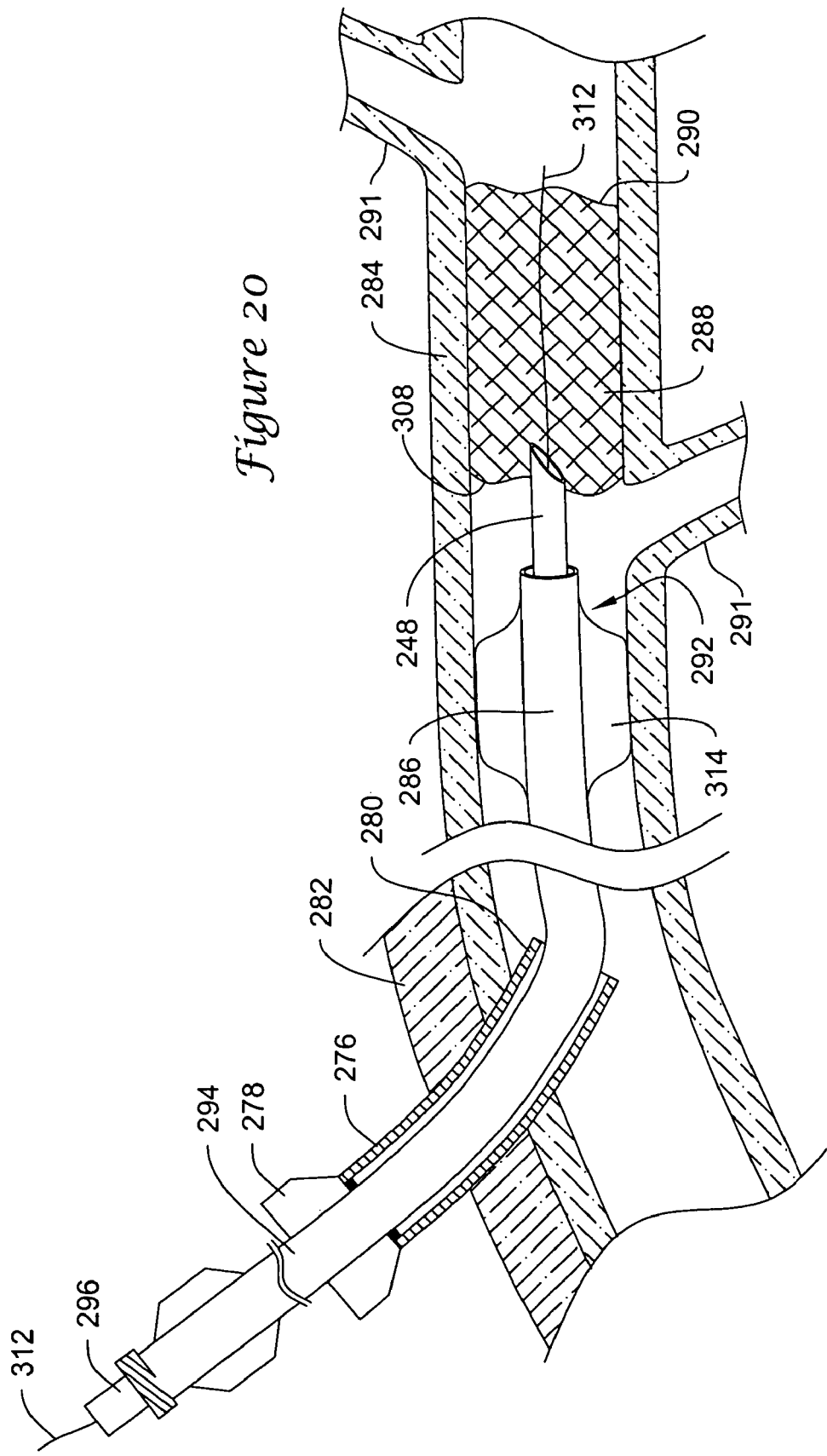

As seen in FIG. 16, the stylet 300 can be moved distally such that the distal region 304 of the stylet 300 penetrates at least partially into the occlusion 288. The stylet 300 can be axially moved back and forth to aid in penetrating the occlusion 288. In some embodiments, the stylet 300 can be rotated and in other embodiments the stylet 300 can be both rotated and moved reciprocally. In some embodiments, the occlusion 288 can have a stiff or otherwise tough proximal cap 308 and a relatively softer central portion 310. In some embodiments, forcing the stylet 300 to penetrate the proximal cap 308 of the occlusion 288 is sufficient to permit a guidewire 312 to be extended through the stylet 300, and then into and through the occlusion 288, as illustrated in FIG. 17. After the stylet has extended through the proximal cap 308, a guidewire 312 can cross through the second sheath as in FIG. 18 or the shaft extension 222 as in FIG. 19 or through the hollow stylet 248 as in FIG. 20. The recanalization assembly can be further advanced through occlusion 288 and the balloon 70 placed near the distal cap 290 and the stylet centered and passed across the distal cap 290 as in FIG. 21. Contrast in section can be made either through the dilation catheter, the second sheath, or the hollow stylet to provide visualization.

As noted, the medical devices in accordance with the present invention can be of conventional materials and construction, except as described herein. The medical devices described herein can be partially or completely coated with a lubricious or other type of coating. Hydrophobic coatings such as fluoropolymers provide a dry lubricity that can improve handling and device exchanges. An example of a suitable fluoropolymer is polytetrafluoroethylene (PTFE), better known as TEFLON®.

Lubricious coatings can improve steerability and improve lesion crossing capability. Examples of suitable lubricious polymers include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers can be blended among themselves or with formulated amounts of water insoluble compounds (including some polymers) to yield coatings with suitable lubricity, bonding, and solubility. In some embodiments, a distal portion of a composite medical device can be coated with a hydrophilic polymer as discussed above, while the more proximal portions can be coated with a fluoropolymer.

The medical devices described herein can include, or be doped with, radiopaque material to improve visibility when using imaging techniques such as fluoroscopy techniques. Any suitable radiopaque material known in the art can be used. Some examples include precious metals, tungsten, barium subcarbonate powder, and the like, and mixtures thereof. In some embodiments, radiopaque material can be dispersed within the polymers used to form the particular medical device. In some embodiments, the radiopaque materials distinct from the ferromagnetic materials are dispersed.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What we claim is:

1. A method of traversing a vascular occlusion using an apparatus comprising an elongate sheath and a stylet captively disposed within the elongate sheath such that relative movement between the sheath and the stylet is limited in both a proximal and a distal direction, the apparatus having a distal region and a proximal region, the stylet having a distal region comprising a cutting surface, the method comprising steps of:
   positioning the apparatus such that its distal region is proximate an occlusion;
   advancing the stylet distally such that its distal region extends distally beyond the distal region of the elongate sheath and contacts a surface of the occlusion;
   moving the stylet such that its cutting surface contacts and penetrates the occlusion; and extending a guidewire through the stylet and through the occlusion.

2. The method of claim 1, wherein the vascular occlusion comprises a total occlusion having a stiff proximal cap.

3. The method of claim 1, wherein moving the stylet comprises rotational motion.

4. The method of claim 1, wherein moving the stylet comprises relative axial motion.

5. The method of claim 4, wherein relative axial motion results from first displacing a spring from its equilibrium position and then releasing the spring.

6. The method of claim 1, further comprising a step of disposing a second sheath over the stylet.

7. The method of claim 1, wherein the apparatus is disposed within a balloon catheter and the balloon is inflated prior to extending the stylet distally.

8. The method of claim 1, wherein the stylet is shorter than the elongate sheath, and the stylet is extended distally via a separate pushing rod or tube disposed within the elongate sheath proximally of the stylet and moveable with respect to the stylet.

9. The method of claim 1 wherein the cutting surface comprises a needle tip.

* * * * *